United States Patent
Armour

(10) Patent No.: US 9,206,418 B2
(45) Date of Patent: Dec. 8, 2015

(54) COMPOSITIONS AND METHODS FOR DIRECTIONAL NUCLEIC ACID AMPLIFICATION AND SEQUENCING

(71) Applicant: NuGEN Technologies, Inc., San Carlos, CA (US)

(72) Inventor: Christopher Armour, Kirkland, WA (US)

(73) Assignee: NUGEN TECHNOLOGIES, INC., San Carlos, CA (US)

( * ) Notice: Subject to any disclaimer, the term of this patent is extended or adjusted under 35 U.S.C. 154(b) by 0 days.

(21) Appl. No.: 13/643,056

(22) PCT Filed: Oct. 19, 2012

(86) PCT No.: PCT/US2012/061218
§ 371 (c)(1),
(2) Date: Oct. 23, 2012

(87) PCT Pub. No.: WO2013/059746
PCT Pub. Date: Apr. 25, 2013

(65) Prior Publication Data
US 2014/0303000 A1    Oct. 9, 2014

Related U.S. Application Data

(60) Provisional application No. 61/549,162, filed on Oct. 19, 2011.

(51) Int. Cl.
*C12N 15/10* (2006.01)
*C12Q 1/68* (2006.01)
*C12N 15/66* (2006.01)

(52) U.S. Cl.
CPC ........ *C12N 15/1096* (2013.01); *C12N 15/1093* (2013.01); *C12N 15/66* (2013.01); *C12Q 1/6806* (2013.01); *C12Q 1/6869* (2013.01)

(58) Field of Classification Search
None
See application file for complete search history.

(56) References Cited

U.S. PATENT DOCUMENTS

| | | | |
|---|---|---|---|
| 4,362,867 A | 12/1982 | Paddock | |
| 4,469,863 A | 9/1984 | Ts'o et al. | |
| 4,582,877 A | 4/1986 | Fairchok et al. | |
| 4,876,187 A | 10/1989 | Duck et al. | |
| 4,935,357 A | 6/1990 | Szybalski | |
| 4,942,124 A | 7/1990 | Church | |
| 4,988,617 A | 1/1991 | Landegren et al. | |

(Continued)

FOREIGN PATENT DOCUMENTS

| | | |
|---|---|---|
| CA | 2444926 A1 | 11/2002 |
| EP | 0365627 B1 | 5/1990 |

(Continued)

OTHER PUBLICATIONS

U.S. Appl. No. 13/938,059, filed Jul. 9, 2013, Schroeder et al.

(Continued)

*Primary Examiner* — Tracy Vivlemore
*Assistant Examiner* — Karen S Weiler
(74) *Attorney, Agent, or Firm* — Wilson Sonsini Goodrich & Rosati

(57) ABSTRACT

The invention provides methods and compositions, including kits, for directional nucleic acid amplification and sequencing. The invention further provides methods and compositions for the construction of directional cDNA libraries.

30 Claims, 4 Drawing Sheets

Construction of directional (strand-specific) cDNA libraries using duplex adaptors: Strand marking of both cDNA and one adaptor results in directional library construction.

The asterisks in the diagram (*) indicate dUTP incorporation.

(56) References Cited

U.S. PATENT DOCUMENTS

| | | |
|---|---|---|
| 4,996,143 A | 2/1991 | Heller et al. |
| 5,011,769 A | 4/1991 | Duck et al. |
| 5,034,506 A | 7/1991 | Summerton et al. |
| 5,035,996 A | 7/1991 | Hartley |
| 5,043,272 A | 8/1991 | Hartley |
| 5,082,830 A | 1/1992 | Brakel et al. |
| 5,090,591 A | 2/1992 | Long |
| 5,130,238 A | 7/1992 | Malek et al. |
| 5,169,766 A | 12/1992 | Schuster et al. |
| 5,171,534 A | 12/1992 | Smith et al. |
| 5,194,370 A | 3/1993 | Berninger et al. |
| 5,216,141 A | 6/1993 | Benner |
| 5,234,809 A | 8/1993 | Boom et al. |
| 5,235,033 A | 8/1993 | Summerton et al. |
| 5,242,794 A | 9/1993 | Whiteley et al. |
| 5,386,023 A | 1/1995 | Sanghvi et al. |
| 5,399,491 A | 3/1995 | Kucian et al. |
| 5,409,818 A | 4/1995 | Davey et al. |
| 5,418,149 A | 5/1995 | Gelfand et al. |
| 5,427,929 A | 6/1995 | Richards et al. |
| 5,480,784 A | 1/1996 | Kacian et al. |
| 5,494,810 A | 2/1996 | Barany et al. |
| 5,508,169 A | 4/1996 | Deugau et al. |
| 5,508,178 A | 4/1996 | Rose et al. |
| 5,510,270 A | 4/1996 | Fodor et al. |
| 5,545,522 A | 8/1996 | Van Gelder et al. |
| 5,554,516 A | 9/1996 | Kacian et al. |
| 5,554,517 A | 9/1996 | Davey et al. |
| 5,556,752 A | 9/1996 | Lockhart et al. |
| 5,565,340 A | 10/1996 | Chenchik et al. |
| 5,573,913 A | 11/1996 | Rosemeyer et al. |
| 5,578,832 A | 11/1996 | Trulson et al. |
| 5,589,339 A | 12/1996 | Hampson et al. |
| 5,602,240 A | 2/1997 | De Mesmaeker et al. |
| 5,637,684 A | 6/1997 | Cook et al. |
| 5,641,658 A | 6/1997 | Adams et al. |
| 5,644,048 A | 7/1997 | Yau et al. |
| 5,665,549 A | 9/1997 | Pinkel et al. |
| 5,667,976 A | 9/1997 | Van Ness et al. |
| 5,667,979 A | 9/1997 | Berrens |
| 5,679,512 A | 10/1997 | Laney et al. |
| 5,681,726 A | 10/1997 | Huse et al. |
| 5,683,879 A | 11/1997 | Laney et al. |
| 5,688,648 A | 11/1997 | Mathies et al. |
| 5,705,628 A | 1/1998 | Hawkins |
| 5,708,154 A | 1/1998 | Smith et al. |
| 5,710,028 A | 1/1998 | Eyal et al. |
| 5,712,126 A | 1/1998 | Weissmann et al. |
| 5,716,785 A | 2/1998 | Van Gelder et al. |
| 5,726,329 A | 3/1998 | Jones et al. |
| 5,750,341 A | 5/1998 | Macevicz |
| 5,759,822 A | 6/1998 | Chenchik et al. |
| 5,763,178 A | 6/1998 | Chirikjian et al. |
| 5,789,206 A | 8/1998 | Tavtigian et al. |
| 5,824,517 A | 10/1998 | Cleuziat et al. |
| 5,824,518 A | 10/1998 | Kacian et al. |
| 5,837,832 A | 11/1998 | Chee et al. |
| 5,876,976 A | 3/1999 | Richards et al. |
| 5,882,867 A | 3/1999 | Ullman et al. |
| 5,888,779 A | 3/1999 | Kacian et al. |
| 5,888,819 A | 3/1999 | Goelet et al. |
| 5,945,313 A | 8/1999 | Hartley et al. |
| 5,952,176 A | 9/1999 | McCarthy et al. |
| 5,958,681 A | 9/1999 | Wetmur et al. |
| 5,965,409 A | 10/1999 | Pardee et al. |
| 5,969,119 A | 10/1999 | Macevicz |
| 5,972,618 A | 10/1999 | Bloch |
| 6,004,744 A | 12/1999 | Goelet et al. |
| 6,004,745 A | 12/1999 | Arnold, Jr. et al. |
| 6,027,889 A | 2/2000 | Barany et al. |
| 6,027,923 A | 2/2000 | Wallace |
| 6,030,774 A | 2/2000 | Laney et al. |
| 6,037,152 A | 3/2000 | Richards et al. |
| 6,056,661 A | 5/2000 | Schmidt |
| 6,077,674 A | 6/2000 | Schleifer et al. |
| 6,087,103 A | 7/2000 | Burmer |
| 6,090,553 A | 7/2000 | Matson |
| 6,090,591 A | 7/2000 | Berg et al. |
| 6,107,023 A | 8/2000 | Reyes et al. |
| 6,110,709 A | 8/2000 | Ausubel et al. |
| 6,150,112 A | 11/2000 | Weissmann et al. |
| 6,159,685 A | 12/2000 | Pinkel et al. |
| 6,160,105 A | 12/2000 | Cunningham et al. |
| 6,169,194 B1 | 1/2001 | Thompson et al. |
| 6,172,208 B1 | 1/2001 | Cook |
| 6,174,680 B1 | 1/2001 | Makrigiorgos |
| 6,190,865 B1 | 2/2001 | Jendrisak et al. |
| 6,194,211 B1 | 2/2001 | Richards et al. |
| 6,197,557 B1 | 3/2001 | Makarov et al. |
| 6,210,891 B1 | 4/2001 | Nyren et al. |
| 6,225,109 B1 | 5/2001 | Juncosa et al. |
| 6,225,451 B1 | 5/2001 | Ballinger et al. |
| 6,232,104 B1 | 5/2001 | Lishanski et al. |
| 6,251,639 B1 | 6/2001 | Kurn |
| 6,262,490 B1 | 7/2001 | Hsu et al. |
| 6,270,961 B1 | 8/2001 | Drmanac |
| 6,280,935 B1 | 8/2001 | Maceivicz |
| 6,287,766 B1 | 9/2001 | Nolan et al. |
| 6,287,825 B1 | 9/2001 | Weissmann et al. |
| 6,291,170 B1 | 9/2001 | Van Gelder et al. |
| 6,306,365 B1 | 10/2001 | Ruoslahti et al. |
| 6,306,597 B1 | 10/2001 | Macevicz |
| 6,309,843 B1 | 10/2001 | Timms |
| 6,326,142 B1 | 12/2001 | Royer |
| 6,335,167 B1 | 1/2002 | Pinkel et al. |
| 6,339,147 B1 | 1/2002 | Luktanov et al. |
| 6,440,705 B1 | 8/2002 | Stanton, Jr. et al. |
| 6,449,562 B1 | 9/2002 | Chandler et al. |
| 6,582,938 B1 | 6/2003 | Su et al. |
| 6,670,461 B1 | 12/2003 | Wengel et al. |
| 6,686,156 B2 | 2/2004 | Kurn |
| 6,692,918 B2 | 2/2004 | Kurn |
| 6,770,748 B2 | 8/2004 | Imanishi et al. |
| 6,777,180 B1 | 8/2004 | Fisher et al. |
| 6,794,499 B2 | 9/2004 | Wengel et al. |
| 6,815,164 B2 | 11/2004 | Kurn |
| 6,815,167 B2 | 11/2004 | Crothers et al. |
| 6,825,011 B1 | 11/2004 | Romantchikov |
| 6,833,246 B2 | 12/2004 | Balasubramanian |
| 6,849,404 B2 | 2/2005 | Park et al. |
| 6,858,413 B2 | 2/2005 | Kurn |
| 6,917,726 B2 | 7/2005 | Levene et al. |
| 6,924,104 B2 | 8/2005 | Weissmann et al. |
| 6,946,251 B2 | 9/2005 | Kurn |
| 7,001,724 B1 | 2/2006 | Greenfield |
| 7,033,764 B2 | 4/2006 | Korlach et al. |
| 7,048,481 B2 | 5/2006 | Sugata et al. |
| 7,052,847 B2 | 5/2006 | Korlach et al. |
| 7,056,676 B2 | 6/2006 | Korlach et al. |
| 7,060,441 B2 | 6/2006 | Bourget et al. |
| 7,094,536 B2 | 8/2006 | Kurn |
| 7,170,050 B2 | 1/2007 | Turner |
| 7,176,025 B2 | 2/2007 | Kurn et al. |
| 7,189,512 B2 | 3/2007 | Porat et al. |
| 7,211,390 B2 | 5/2007 | Rothberg et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,273,730 B2 | 9/2007 | Du Breuil Lastrucci |
| 7,276,720 B2 | 10/2007 | Ulmer |
| 7,300,755 B1 | 11/2007 | Petersdorf et al. |
| 7,302,146 B2 | 11/2007 | Turner et al. |
| 7,313,308 B2 | 12/2007 | Turner et al. |
| 7,315,019 B2 | 1/2008 | Turner et al. |
| 7,323,305 B2 | 1/2008 | Leamon et al. |
| 7,335,762 B2 | 2/2008 | Rothberg et al. |
| 7,361,466 B2 | 4/2008 | Korlach et al. |
| 7,361,468 B2 | 4/2008 | Liu et al. |
| 7,402,386 B2 | 7/2008 | Kurn et al. |
| 7,405,281 B2 | 7/2008 | Xu et al. |
| 7,414,117 B2 | 8/2008 | Saito et al. |
| 7,416,844 B2 | 8/2008 | Korlach et al. |
| 7,462,452 B2 | 12/2008 | Williams et al. |
| 7,462,468 B1 | 12/2008 | Williams et al. |

(56) References Cited

U.S. PATENT DOCUMENTS

| | | |
|---|---|---|
| 7,476,503 B2 | 1/2009 | Turner et al. |
| 7,476,504 B2 | 1/2009 | Turner |
| 7,491,498 B2 | 2/2009 | Lapidus et al. |
| 7,501,245 B2 | 3/2009 | Quake et al. |
| 7,579,153 B2 | 8/2009 | Brenner et al. |
| 7,741,463 B2 | 6/2010 | Gormley et al. |
| 7,803,550 B2 | 9/2010 | Makarov et al. |
| 8,017,335 B2 | 9/2011 | Smith |
| 8,053,192 B2 | 11/2011 | Bignell et al. |
| 8,143,001 B2 | 3/2012 | Kurn et al. |
| 2001/0000077 A1 | 3/2001 | Engelhardt et al. |
| 2001/0031739 A1 | 10/2001 | Dare |
| 2001/0034048 A1 | 10/2001 | Kurn |
| 2001/0041334 A1 | 11/2001 | Rashtchian et al. |
| 2002/0028447 A1 | 3/2002 | Li et al. |
| 2002/0058270 A1 | 5/2002 | Kurn |
| 2002/0115088 A1 | 8/2002 | Kurn |
| 2002/0150919 A1 | 10/2002 | Weismann et al. |
| 2002/0155451 A1 | 10/2002 | Makrigiorgos |
| 2002/0164628 A1 | 11/2002 | Kurn |
| 2002/0164634 A1 | 11/2002 | Patil et al. |
| 2002/0197639 A1 | 12/2002 | Shia et al. |
| 2003/0017591 A1 | 1/2003 | Kurn |
| 2003/0022207 A1 | 1/2003 | Balasubramanian et al. |
| 2003/0082543 A1 | 5/2003 | Su et al. |
| 2003/0087251 A1 | 5/2003 | Kurn |
| 2003/0119150 A1 | 6/2003 | Ankenbauer et al. |
| 2003/0143555 A1 | 7/2003 | Bourget et al. |
| 2003/0175780 A1 | 9/2003 | Jones |
| 2003/0180779 A1 | 9/2003 | Lofton-Day et al. |
| 2003/0186234 A1 | 10/2003 | Kurn |
| 2003/0207279 A1 | 11/2003 | Crothers et al. |
| 2003/0215926 A1 | 11/2003 | Kurn et al. |
| 2003/0224439 A1 | 12/2003 | Lafferty et al. |
| 2003/0232348 A1 | 12/2003 | Jones et al. |
| 2004/0002371 A1 | 1/2004 | Paquine et al. |
| 2004/0005614 A1 | 1/2004 | Kurn et al. |
| 2004/0023271 A1 | 2/2004 | Kurn et al. |
| 2004/0115815 A1 | 6/2004 | Li et al. |
| 2004/0137456 A1 | 7/2004 | Yokota et al. |
| 2004/0161742 A1 | 8/2004 | Dean et al. |
| 2004/0203019 A1 | 10/2004 | Kurn |
| 2004/0203025 A1 | 10/2004 | Kurn |
| 2004/0248153 A1 | 12/2004 | Dear et al. |
| 2005/0003441 A1 | 1/2005 | Kurn |
| 2005/0014192 A1 | 1/2005 | Kurn |
| 2005/0019793 A1 | 1/2005 | Kurn et al. |
| 2005/0059048 A1 | 3/2005 | Gunderson et al. |
| 2005/0064456 A1 | 3/2005 | Kurn |
| 2005/0123956 A1 | 6/2005 | Blume et al. |
| 2005/0136417 A1 | 6/2005 | Cole et al. |
| 2005/0142577 A1 | 6/2005 | Jones et al. |
| 2005/0191656 A1 | 9/2005 | Drmanac et al. |
| 2005/0191682 A1 | 9/2005 | Barone et al. |
| 2005/0208538 A1 | 9/2005 | Kurn et al. |
| 2006/0008824 A1 | 1/2006 | Ronaghi et al. |
| 2006/0014182 A1 | 1/2006 | Kurn |
| 2006/0024678 A1 | 2/2006 | Buzby |
| 2006/0024711 A1 | 2/2006 | Lapidus et al. |
| 2006/0035274 A1 | 2/2006 | Dong |
| 2006/0046251 A1 | 3/2006 | Sampson et al. |
| 2006/0051789 A1 | 3/2006 | Kazakov et al. |
| 2006/0216724 A1 | 9/2006 | Christians et al. |
| 2006/0263789 A1 | 11/2006 | Kincaid |
| 2006/0281082 A1 | 12/2006 | Zhu |
| 2006/0286566 A1 | 12/2006 | Lapidus et al. |
| 2006/0292597 A1 | 12/2006 | Shapero et al. |
| 2007/0031857 A1 | 2/2007 | Makarov et al. |
| 2007/0134128 A1 | 6/2007 | Korlach |
| 2007/0224613 A1 | 9/2007 | Strathmann |
| 2007/0231823 A1 | 10/2007 | McKernan et al. |
| 2007/0238122 A1 | 10/2007 | Allbritton et al. |
| 2008/0038727 A1 | 2/2008 | Spier |
| 2008/0087826 A1 | 4/2008 | Harris et al. |
| 2008/0103058 A1 | 5/2008 | Siddiqi |
| 2008/0176311 A1 | 7/2008 | Kurn |
| 2008/0182300 A1 | 7/2008 | Kurn |
| 2008/0194413 A1 | 8/2008 | Albert |
| 2008/0194416 A1 | 8/2008 | Chen |
| 2008/0206764 A1 | 8/2008 | Williams et al. |
| 2008/0213770 A1 | 9/2008 | Williams et al. |
| 2008/0242560 A1 | 10/2008 | Gunderson et al. |
| 2008/0286795 A1 | 11/2008 | Kawashima et al. |
| 2009/0011959 A1 | 1/2009 | Costa et al. |
| 2009/0024331 A1 | 1/2009 | Tomaney et al. |
| 2009/0026082 A1 | 1/2009 | Rothberg et al. |
| 2009/0029385 A1 | 1/2009 | Christians et al. |
| 2009/0061425 A1 | 3/2009 | Lo et al. |
| 2009/0061439 A1 | 3/2009 | Buzby |
| 2009/0068645 A1 | 3/2009 | Sibson |
| 2009/0068655 A1 | 3/2009 | Williams |
| 2009/0068709 A1 | 3/2009 | Kurn et al. |
| 2009/0117573 A1 | 5/2009 | Fu et al. |
| 2009/0117621 A1 | 5/2009 | Boutell et al. |
| 2009/0124514 A1 | 5/2009 | Fu et al. |
| 2009/0130721 A1 | 5/2009 | Kurn et al. |
| 2009/0203085 A1 | 8/2009 | Kurn et al. |
| 2009/0203531 A1 | 8/2009 | Kurn et al. |
| 2009/0239232 A1 | 9/2009 | Kurn et al. |
| 2009/0275486 A1 | 11/2009 | Kurn et al. |
| 2009/0280538 A1 | 11/2009 | Patel et al. |
| 2009/0298075 A1 | 12/2009 | Travers et al. |
| 2010/0015666 A1 | 1/2010 | Brenner et al. |
| 2010/0021973 A1 | 1/2010 | Makarov et al. |
| 2010/0022403 A1 | 1/2010 | Kurn et al. |
| 2010/0029511 A1 | 2/2010 | Raymond et al. |
| 2010/0105052 A1 | 4/2010 | Drmanac et al. |
| 2010/0113296 A1 | 5/2010 | Myerson |
| 2010/0129879 A1 | 5/2010 | Ach et al. |
| 2010/0137143 A1 | 6/2010 | Rothberg et al. |
| 2010/0167954 A1 | 7/2010 | Earnshaw et al. |
| 2010/0173394 A1 | 7/2010 | Colston, Jr. et al. |
| 2010/0273219 A1 | 10/2010 | May et al. |
| 2010/0323348 A1 | 12/2010 | Hamady et al. |
| 2011/0039732 A1 | 2/2011 | Raymond et al. |
| 2011/0104785 A1 | 5/2011 | Vaidyanathan et al. |
| 2011/0105364 A1 | 5/2011 | Kurn |
| 2011/0129827 A1 | 6/2011 | Causey et al. |
| 2011/0189679 A1 | 8/2011 | Kurn et al. |
| 2011/0224105 A1 | 9/2011 | Kurn et al. |
| 2011/0288780 A1 | 11/2011 | Rabinowitz et al. |
| 2012/0045797 A1 | 2/2012 | Kurn et al. |
| 2012/0071331 A1 | 3/2012 | Casbon et al. |
| 2012/0074925 A1 | 3/2012 | Oliver |
| 2012/0102054 A1 | 4/2012 | Popescu et al. |
| 2012/0122701 A1 | 5/2012 | Ryan et al. |
| 2012/0157322 A1 | 6/2012 | Myllykangas et al. |
| 2012/0220483 A1 | 8/2012 | Kurn et al. |
| 2012/0237943 A1 | 9/2012 | Soldatov et al. |
| 2012/0245041 A1 | 9/2012 | Brenner et al. |
| 2012/0270212 A1 | 10/2012 | Rabinowitz et al. |
| 2012/0283145 A1 | 11/2012 | Wang |
| 2012/0309002 A1 | 12/2012 | Link |
| 2013/0059738 A1 | 3/2013 | Leamon et al. |
| 2013/0231253 A1 | 9/2013 | Amorese et al. |
| 2014/0065692 A1 | 3/2014 | Kurn et al. |
| 2014/0274729 A1 | 9/2014 | Kurn et al. |
| 2014/0274731 A1 | 9/2014 | Raymond et al. |
| 2014/0274738 A1 | 9/2014 | Amorese et al. |
| 2014/0378345 A1 | 12/2014 | Hindson et al. |
| 2015/0011396 A1 | 1/2015 | Schroeder et al. |
| 2015/0017635 A1 | 1/2015 | Myllykangas et al. |

FOREIGN PATENT DOCUMENTS

| | | |
|---|---|---|
| EP | 0329822 B1 | 6/1994 |
| EP | 0667393 A2 | 8/1995 |
| EP | 0667393 A3 | 11/1995 |
| EP | 1071811 B1 | 3/2002 |
| EP | 0843735 B1 | 7/2002 |
| EP | 2272976 A1 | 1/2011 |
| EP | 2322612 A1 | 5/2011 |
| WO | WO 92/07951 A1 | 5/1992 |
| WO | WO 93/18052 A1 | 9/1993 |

(56) References Cited

FOREIGN PATENT DOCUMENTS

| | | |
|---|---|---|
| WO | WO 94/16090 A1 | 7/1994 |
| WO | WO 97/12061 A1 | 4/1997 |
| WO | WO 97/25416 A2 | 7/1997 |
| WO | WO 97/25416 A3 | 10/1997 |
| WO | WO 98/06736 A1 | 2/1998 |
| WO | WO 98/38296 A1 | 9/1998 |
| WO | WO 98/44151 A1 | 10/1998 |
| WO | WO 99/10540 A1 | 3/1999 |
| WO | WO 99/11819 A1 | 3/1999 |
| WO | WO 99/42618 A1 | 8/1999 |
| WO | WO 00/08208 A2 | 2/2000 |
| WO | WO 00/09756 A1 | 2/2000 |
| WO | WO 00/08208 A3 | 5/2000 |
| WO | WO 00/18957 A1 | 6/2000 |
| WO | WO 00/39345 A1 | 7/2000 |
| WO | WO 00/52191 A1 | 9/2000 |
| WO | WO 00/55364 A2 | 9/2000 |
| WO | WO 01/20035 A2 | 3/2001 |
| WO | WO 01/23613 A1 | 4/2001 |
| WO | WO 01/46464 A1 | 6/2001 |
| WO | WO 01/57248 A2 | 8/2001 |
| WO | WO 01/64952 A2 | 9/2001 |
| WO | WO 00/55364 A3 | 10/2001 |
| WO | WO 01/20035 A3 | 12/2001 |
| WO | WO 02/00938 A2 | 1/2002 |
| WO | WO 01/57248 A3 | 2/2002 |
| WO | WO 02/28876 A2 | 4/2002 |
| WO | WO 02/29117 A2 | 4/2002 |
| WO | WO 02/36821 A2 | 5/2002 |
| WO | WO 02/48402 A2 | 6/2002 |
| WO | WO 02/28876 A3 | 8/2002 |
| WO | WO 02/060318 A2 | 8/2002 |
| WO | WO 02/072772 A2 | 9/2002 |
| WO | WO 02/072773 A2 | 9/2002 |
| WO | WO 02/081753 A1 | 10/2002 |
| WO | WO 02/090584 A2 | 11/2002 |
| WO | WO 01/64952 A3 | 12/2002 |
| WO | WO 03/002736 A2 | 1/2003 |
| WO | WO 03/012118 A1 | 2/2003 |
| WO | WO 02/36821 A3 | 3/2003 |
| WO | WO 03/027259 A2 | 4/2003 |
| WO | WO 02/00938 A3 | 8/2003 |
| WO | WO 02/29117 A3 | 8/2003 |
| WO | WO 02/072772 A3 | 9/2003 |
| WO | WO 02/090584 A3 | 9/2003 |
| WO | WO 03/078645 A2 | 9/2003 |
| WO | WO 02/060318 A3 | 10/2003 |
| WO | WO 03/083435 A2 | 10/2003 |
| WO | WO 02/072773 A3 | 12/2003 |
| WO | WO 03/027259 A3 | 12/2003 |
| WO | WO 03/106642 A2 | 12/2003 |
| WO | WO 2003/083435 A3 | 2/2004 |
| WO | WO 03/078645 A3 | 3/2004 |
| WO | WO 02/48402 A3 | 4/2004 |
| WO | WO 2004/011665 A2 | 9/2004 |
| WO | WO 2003/106642 A3 | 11/2004 |
| WO | WO 2004/011665 A3 | 7/2005 |
| WO | WO 2005/065321 A2 | 7/2005 |
| WO | WO 2006/081222 A2 | 8/2006 |
| WO | WO 2006/081222 A3 | 2/2007 |
| WO | WO 2007/018601 A1 | 2/2007 |
| WO | WO 2007/030759 A2 | 3/2007 |
| WO | WO 2007/057652 A1 | 5/2007 |
| WO | WO 2007/030759 A3 | 6/2007 |
| WO | WO 2007/136717 A1 | 11/2007 |
| WO | WO 2008/005459 A2 | 1/2008 |
| WO | WO 2008/005459 A3 | 2/2008 |
| WO | WO 2008/033442 A2 | 3/2008 |
| WO | WO 2008/115185 A2 | 9/2008 |
| WO | WO 2008/033442 A3 | 10/2008 |
| WO | WO 2008/115185 A3 | 12/2008 |
| WO | WO 2009/053039 A1 | 4/2009 |
| WO | WO 2005/065321 A3 | 5/2009 |
| WO | WO 2009/120372 A2 | 10/2009 |
| WO | WO 2009/120374 A2 | 10/2009 |
| WO | WO 2009/120374 A3 | 12/2009 |
| WO | WO 2009/120372 A3 | 1/2010 |
| WO | WO 2010/003153 A2 | 1/2010 |
| WO | WO 2010/030683 A1 | 3/2010 |
| WO | WO 2010/063711 A1 | 6/2010 |
| WO | WO 2010/064893 A1 | 6/2010 |
| WO | WO 2010/115154 A1 | 10/2010 |
| WO | WO 2010/129937 A2 | 11/2010 |
| WO | WO 2011/003630 A1 | 1/2011 |
| WO | WO 2011/032053 A1 | 3/2011 |
| WO | WO 2012/103154 A1 | 8/2012 |
| WO | WO 2013/059746 A1 | 4/2013 |
| WO | WO 2013/177220 A1 | 11/2013 |

OTHER PUBLICATIONS

U.S. Appl. No. 14/030,761, filed Sep. 18, 2013, Kurn et al.
Office action dated Sep. 25, 2014 for U.S. Appl. No. 13/750,768.
Beaucage, et al. The functionalization of oligonucleotides via phosphoramidite derivative. Tetrahedron. 1993;49(10):1925-63.
Brill, et al. Synthesis of oligodeoxynucleoside phosphorodithioates via thioamidites. J. Am. Chem. Soc. 1989;111:2321-2322.
Carlsson, et al. Screening for genetic mutations. Nature. 1996;380(6571):207.
Dempcy, et al. Synthesis of a thymidyl pentamer of deoxyribonucleic guanidine and binding studies with DNA homopolynucleotides. Proc Natl Acad Sci USA. 1995;92(13):6097-101.
Drmanac, et al. Human genome sequencing using unchained base reads on self-assembling DNA nanoarrays. Science. Jan. 1, 2010;327(5961):78-81. doi: 10.1126/science.1181498. Epub Nov. 5, 2009.
Egholm, et al. Peptide nucleic acids (PNA) oligonucleotide analogues with an achiral peptide backbone. J. Am. Chem. Soc. 1992;114:1895-1897.
Egholm, et al. PNA hybridizes to complementary oligonucleotides obeying the Watson-Crick hydrogen-bonding rules. Nature. 1993;365(6446):566-8.
Jenkins, et al. The biosynthesis of carbocyclic nucleosides. Chem. Soc. Rev. 1995;169-176.
Kiedrowski, et al. Parabolic growth of a self-replicating hexadeoxynucleotide bearing a 3'-5'-phosphoamidate linkage. Angew. Chem. Intl. Ed. English 1991;30:423-426.
Koshkin, et al. LNA (Locked Nucleic Acid): An RNA mimic forming exceedingly stable LNA:LNA duplexes. J. Am. Chem. Soc. 1998; 120:13252-3.
Letsinger, et al. Cationic oligonucletides. J. Am Chem. Soc. 1988; 110:4470-4471.
Letsinger, et al. Effects of pendant groups at phosphorus on binding properties of d-ApA analogues. Nucleic Acids Res. 1986;14(8):3487-99.
Letsinger, et al. Phosphoramidate analogs of oligonucleotides. J Org Chem. 1970;35(11):3800-3.
Mag, et al. Synthesis and selective cleavage of an oligodeoxynucleotide containing a bridged internucleotide 5'-phosphorothioate linkage. Nucleic Acids Res. 1991;19(7):1437-41.
Margulies, et al. Genome sequencing in microfabricated high-density picolitre reactors [abstract]. *Nature*. Sep. 15, 2005; 437 (7057): 376-80. Epub Jul. 31, 2005.
Meier, et al. Peptide nuclieic acids (PNAS)—Unusual properties of nonionic oligonucleotide analogues. Chem. Int. Ed. Engl. 1992;31:1008-1010.
Pauwels, et al. Biological activity of new 2-5A analogues. Chemica Scripta. 1986;26:141-9.
Rawls, R. Optimistic about antisense. Promising clinical results and chemical strategies for further improvements delight antisense drug researchers. C & E News. Jun. 2, 1997; 35-59.
Sanghvi, et al. ed. Chapters 2 and 3, ASC Symposium Series 580—Carbohydrates Modifications in Antisense Research. American Chemical Society. Washington, DC. 1994.
Sanghvi, et al. ed. Chapters 6 and 7, ASC Symposium Series 580—Carbohydrates Modifications in Antisense Research. American Chemical Society. Washington, DC. 1994.

(56) References Cited

OTHER PUBLICATIONS

Sawai, et al. Synthesis and properties of oligoadenylic acids containing 2'-5' phosphoramide linkage. Chem. Lett. 1984; 805-808.
Soni, et al. Progress toward ultrafast DNA sequencing using solid-state nanopores. Clin Chem. Nov. 2007;53(11):1996-2001. Epub Sep. 21, 2007.
Sprinzl, et al. Enzymatic incorporation of ATP and CTP analogues into the 3' end of tRNA. Eur J Biochem. Dec. 1977;81(3):579-89.
Walker, et al., Strand displacement amplification—an isothermal, in vitro DNA amplifcation technique. Nucleic Acids Resarch. 1991. 20(7): 1691-1696.
Westin, et al., Anchored multiplex amplification on a microelectronic chip array Nature Biotechnology. Feb. 2000 18(2):199-204.
Myllykangas, et al. Efficient targeted resequencing of human germline and cancer genomes by oligonucleotide-selective sequencing. Nat Biotechnol. Oct. 23, 2011;29(11):1024-7. doi: 10.1038/nbt.1996.
Borodina, et al. A strand-specific library preparation protocol for RNA sequencing. Chpater 5. Methods in Enzymology. Sep. 20, 2011; 500:79-98.
International search report and written opinion dated Feb. 12, 2013 for PCT/US2012/061218.
Office action dated Jul. 13, 2007 for U.S. Appl. No. 11/026,280.
Office action dated Apr. 16, 2014 for U.S. Appl. No. 13/239,226.
Office action dated Sep. 24, 2014 for U.S. Appl. No. 13/239,226.
Briggs, et al. Targeted retrieval and analysis of five Neandertal mtDNA genomes. Science. Jul. 17, 2009;325(5938):318-21. doi: 10.1126/science.1174462.
Karow. New Capture Method Enables MPI Team to Sequence Five Neandertal Mitochondrial Genomes. GenomeWeb. Jul. 21, 2009. https://www.genomeweb.com/sequencing/new-capture-method-enables-mpi-team-sequence-five-neandertal-mitochondrial-genom.
U.S. Appl. No. 14/390,012, filed Oct. 1, 2014, Armour et al.
U.S. Appl. No. 14/634,326, filed Feb. 27, 2015, Schroeder.
Ahmed. Sequencing of Low-Diversity Libraries. Feb. 28, 2012. http://cofactorgenomics.com/sequencing-low-diversity-libraries/.
Diagnosing problems with phasing and pre-phasing on Illumina platforms. Loman Labs. Nov. 21, 2013. http://nickloman.github.io/high-throughput%20sequencing/2013/11/21/diagnosing-problems-with-phasing-and-pre-phasing-on-illumina-platforms/.
Fadrosh, et al. An improved dual-indexing approach for multiplexed 16S rRNA gene sequencing on the Illumina MiSeq platform. Microbiome. Feb. 24, 2014;2(1):6. doi: 10.1186/2049-2618-2-6.
Faircloth, et al. Not all sequence tags are created equal: designing and validating sequence identification tags robust to indels. PLoS One. 2012;7(8):e42543. doi: 10.1371/journal.pone.0042543. Epub Aug. 10, 2012.
Gu, et al. Preparation of reduced representation bisulfite sequencing libraries for genome-scale DNA methylation profiling. Nat Protoc. Apr. 2011;6(4):468-81. doi: 10.1038/nprot.2010.190. Epub Mar. 18, 2011.
Kozich, et al. Development of a dual-index sequencing strategy and curation pipeline for analyzing amplicon sequence data on the MiSeq Illumina sequencing platform. Appl Environ Microbiol. Sep. 2013;79(17):5112-20. doi: 10.1128/AEM.01043-13. Epub Jun. 21, 2013.
Krueger, et al. Large scale loss of data in low-diversity illumina sequencing libraries can be recovered by deferred cluster calling. PLoS One. Jan. 28, 2011;6(1):e16607. doi: 10.1371/journal.pone.0016607.
Krueger. Loss of data in low-diversity libraries can be recovered by deferred cluster calling. Poster Jan. 29, 2011. http://seqanswers.com/forums/showthread.php?t=9150.
Leonard. What is a reliable method for multiplexing more than 384 samples on a MiSeq run? Posted Aug. 19, 2013. http://www.researchgate.net/post/What_is_a_reliable_method_for_multiplexing_more_than_384_samples_on_a_MiSeq_run2.
Nextera® Rapid Capture Enrichment Low-Plex Pooling Guidelines. Technical Note: DNA Analysis. 2014. http://www.illumina.com/content/dam/illumina-marketing/documents/products/technotes/technote-nextera-rapid-capture-low-plex-pooling-guidelines.pdf.
Office action dated Mar. 9, 2015 for CN Application No. 201380006942.4.
SEQanswers. MiSeq cluster generation problems. Posted Mar. 17, 2012. http://seqanswers.com/forums/showthread.php?t=18499.
SEQanswers. Sequencing a Low diversity library on the HiSeq. Posted Nov. 18, 2011. http://seqanswers.com/forums/showthread.php?t=18499.
Singapore written opinion dated Mar. 17, 2015 for SG Application No. 11201401628W.
Wu, et al. Phasing Amplicon Sequencing for Robust Microbial Community Analysis. I-2630. 2014. http://www.asmonlineeducation.com/php/asm2014abstracts/data/papers/I-2630.htm.
U.S. Appl. No. 13/980,987, filed Jul. 22, 2013, Kurn et al.
U.S. Appl. No. 14/211,261, filed Mar. 14, 2014, Amorese et al.
AB Applied Biosystems. The solid 3 system enabling the next generation of science. Presentation. 2009.
Adessi, et al., Solid phase DNA amplification: characterisation of primer attachment and ampflication mechanisms. Nucleic Acids Research. Oct. 15, 2000 28:(20): e87.
Agilent Technologies. Agilent Technologies adds human exon kit to next-generation-sequencing target enrichment portfolio. GenomicsNews.com. Posted Sep. 23, 2009. Avaialble at http://www.genomicsnews.com/index.aspx?ID=103607&sm=Agilent%20technologies%20adds%20human%20exo. Accessed Oct. 6, 2009.
Albert, et al. Direct selection of human genomic loci by microarray hybridization. Nat Methods. Nov. 2007;4(11):903-5. Epub Oct. 14, 2007.
Anisimova, et al. Isolation, characterization and molecular cloning of duplex-specific nuclease from the hepatopancreas of the kamchatka crab. *BMC Biochemistry*. May 21, 2008. 9:14 doi10.1186/1471-2091-9-14.
Antson, et al. PCR-generated padlock probes detect single nucleotide variation in genomic DNA. Nucleic Acids Res. Jun. 15, 2000;28(12):E58.
Anwar, et al. A stem-loop-mediated reverse transcription real-time PCR for the selective detection and quantification of the replicative strand of an RNA virus. Anal Biochem. May 1, 2006;352(1):120-8. Epub Feb. 17, 2006.
Arraystar, Inc. Arraystar Directional RNA-seq Prep Kit (dUTP Based). Cat#: A1208. Apr. 8, 2013.
Baird, et al. Rapid SNP discovery and genetic mapping using sequenced RAD markers. PLoS One. 2008;3(10):e3376.
Bashiardes, et al. Direct genomic selection. Nat Methods. Jan. 2005;2(1):63-9.
Beier, et al. HT sequencing in biomedicine—new approaches in preparing samples. *Laborwelt*. Jan. 9, 2008.
Bentley, D. R. Whole-genome re-sequencing. Curr Opin Genet Dev. Dec. 2006;16(6):545-52. Epub Oct. 18, 2006.
Bhattacharjee, et al. Complementing next generation sequencing technologies with Agilent's SureSelect DNA capture array. Agilent. Jul. 13, 2009.
Bibikova, et al. Targeted chromosomal cleavage and mutagenesis in drophila using zinc-finger nucleases genetics. *Genetics*. Jul. 2002. 161: 1169-1175.
Bioo Scientific. Illumina RNA-Seq Library Prep. Available at http://www.biooscientific.com/ProductsServices/NextGenSequencing/Illumina-Compatible/RNA-Seq.aspx. Accessed Jun. 16, 2014.
Bioo Scientific. NEXTflex RNA-Seq Kit. Available at http://www.biooscientific.com/ProductsServices/NextGenSequencing/Illumina-Compatible/RNA-Seq/NEXTflex%E2%84%A2RNA-SeqKit.aspx. Accessed Jun. 16, 2014.
Blow, N. Genomics: catch me if you can. *Nature Methods*. Jul. 2009. 6:7.539-544.
Bormann, et al. Whole methylome analysis by ultra-deep sequencing using two-base encoding PLoS One. Feb. 22, 2010;5(2):e9320.
Borodina, et al. A strand-specific library preparation protocol for RNA sequencing. Methods Enzymol. 2011;500:79-98. doi: 10.1016/B978-0-12-385118-5.00005-0.

(56) References Cited

OTHER PUBLICATIONS

Broude. Stem-loop oligonucleotides: a robust tool for molecular biology and biotechnology. Trends Biotechnol. Jun. 2002;20(6):249-56.
Chen, et al. Real-time quantification of microRNAs by stem-loop RT-PCR. Nucleic Acids Res. Nov. 27, 2005;33(20):e179.
Clontech Laboratories, Inc. In-Fusion SMARTer Directional cDNA Library Construction Kit User Manual. Cat. No. 634933. Copyright 2013.
Cofactor genomics. Directional RNA Sequencing. Abailable at http://cofactorgenomics.com/directional-rna-sequencing. Accessed Jun. 4, 2014.
Craig, et al. Identification of genetic variants using bar-coded multiplexed sequencing. Nat Methods. Oct. 2008;5(10):887-93.
Croucher, et al. A simple method for directional transcriptome sequencing using Illumina technology. Nucleic Acids Res. Dec. 2009;37(22):e148.
Dahl, et al. Multigene amplification and massively parallel sequencing for cancer mutation discovery. Proc Natl Acad Sci U S A. May 29, 2007;104(22):9387-92. Epub May 17, 2007.
Dahl, et al. Multiplex amplification enabled by selective circularization of large sets of genomic DNA fragments. Nucleic Acids Res. Apr. 28, 2005;33(8):e71.
Dressman, et al., Transforming single DNA molecules into fluorescent magnetic particles for detection and enumeration of genetic variations. Proc Natl Sci USA. Jul. 22, 2003. 100(15): 8817-8822.
Esteller. Cancer epigenomics: DNA methylomes and histone-modification maps. Nat Rev Genet. Apr. 2007;8(4):286-98. Epub Mar. 6, 2007.
European search report and opinion dated Nov. 28, 2013 for EP Application No. 11793123.8.
Fahy, et al., Self-sustained sequence replication (3SR): an isothermal transcription-based amplication system alternative to PCR. Genome Res. 1991. 1:25-33.
Feinberg, et al. Hypomethylation distinguishes genes of some human cancers from their normal counterparts. Nature. Jan. 6, 1983;301(5895):89-92.
Franca, et al. Optimizing a qPCR gene expression quantification assay for *S. epidermidis* biofilms: a comparison between commercial kits and a customized protocol. PLoS One. 2012;7(5):e37480. doi: 10.1371/journal.pone.0037480. Epub May 21, 2012.
Frank. Barcrawl and Bartab: software tools for the design and implementation of barcoded primers for highly multiplexed DNA sequencing. BMC Bioinformatics. Oct. 29, 2009;10:362.
Fredriksson, et al. Multiplex amplification of all coding sequences within 10 cancer genes by Gene-Collector. Nucleic Acids Res. 2007;35(7):e47. Epub Feb. 22, 2007.
Fujiwara, et al. Direct probing: covalent attachment of probe DNA to double-stranded target DNA. Nucleic Acids Res. Dec. 15, 1998;26(24):5728-33.
Fullwood, et al. Next-generation DNA sequencing of paired-end tags (PET) for transcriptome and genome analyses. *Genome Research Open Access*. 2009. Available at http://genome.cshlp.org/content/19/4/521.long. Accessed Oct. 6, 2009.
Gertz, et al. Transposase mediated construction of RNA-seq libraries. Genome Res. Jan. 2012;22(1):134-41. doi: 10.1101/gr.127373.111. Epub Nov. 29, 2011.
Gnirke, et al. Solution hybrid selection with ultra-long oligonucleotides for massively parallel targeted sequencing. Nature Biotechnology. Feb. 2009; 27(2):182-9.
Gu, et al. Partitioning the c. elegans genome by nucleosome modification, occupancy, and position. Online Aug. 25, 2009. http://www.springerlink com/content/r0gw044155823242/fulltext.pdf. Accessed Oct. 6, 2009.
Hodges, et al. Genome-wide in situ exon capture for selective resequencing. Nat Genet. Dec. 2007;39(12):1522-7. Epub Nov. 4, 2007.
Hodges, et al. Hybrid selection of discrete genomic intervals on custom-designed microarrays for massively parallel sequencing. *Nat. Protoc*. 2009; 4(6): 960-974.

Illumina Inc. Directional mRNA-Seq Sample Preparation—Application to prepare directional (strand specific) sample from mRNA. Oct. 2010.
International search report and written opinion dated Jan. 27, 2012 for PCT Application No. US2011/039683.
International search report and written opinion dated Feb. 24, 2011 for PCT Application No. US10/55137.
International search report and written opinion dated Apr. 16, 2013 for PCT Application No. US2013/023278.
International search report and written opinion dated May 10, 2012 for PCT Application No. US2012/22448.
International search report and written opinion dated Oct. 18, 2013 for PCT Application No. US2013/032606.
Jones, et al. The epigenomics of cancer. Cell. Feb. 23, 2007;128(4):683-92.
Kaboev, et al. PCR hot start using primers with the structure of molecular beacons (hairpin-like structure). Nucleic Acids Res. Nov. 1, 2000;28(21):E94.
Krishnakumar, et al. A comprehensive assay for targeted multiplex amplification of human DNA sequences. Proc Natl Acad Sci U S A. Jul. 8, 2008;105(27):9296-301. doi: 10.1073/pnas.0803240105. Epub Jul. 2, 2008.
Krueger, et al. Bismark: a flexible aligner and methylation caller for Bisulfite-Seq applications. Bioinformatics. Jun. 1, 2011;27(11):1571-2. doi: 10.1093/bioinformatics/btr167. Epub Apr. 14, 2011.
Kumar, et al. A High-Throughput Method for Illumina RNA-Seq Library Preparation. Front Plant Sci. Aug. 28, 2012;3:202. doi: 10.3389/fpls.2012.00202. eCollection 2012.
Kurn. Method for generation of double stranded cDNA from RNA targets useful for global amplification, sequencing or other quantification of short RNA in a sample. Mar. 21, 2010. 1-5.
Laird. Principles and challenges of genomewide DNA methylation analysis. Nat Rev Genet. Mar. 2010;11(3):191-203. doi:10.1038/nrg2732.
Lao, et al. Real time PCR profiling of 330 human micro-RNAs. Biotechnol J. Jan. 2007;2(1):33-5.
LC Sciences. Targeted sequencing—sample enrichment service. 2009. Available at www.lcsciences.com/products/genomics/targeted_sequencing/targeted_sequencing.html . Accessed Oct. 6, 2009.
LC Sciences. Technology—Massively parallel oligonucleotide and peptide synthesis on a micrchip based on the uParaflo micro fluidic technology. Available at www.lcsciences.com/support/technology/technology.html. Accessed Oct. 6, 2009.
LC Sciences. Oligonucleotide mixture. OligoMix. 2009. Available at www.lcsciences.com/products/genomics/oligomix/oligomix_detail.html. Accessed Oct. 6, 2009.
Leamon, et al., a Massively parallel Pico TiterPlate based platform for discrete picoliter-scale polymerase chaine reactions [abstract]. *Electrophoresis*. Nov. 24, 2003(21) 3769-77.
Lefrancois, et al. Efficient yeast ChIP-Seq using multiplex short-read DNA sequencing. BMC Genomics. Jan. 21, 2009;10:37.
Lennon, et al. A scalable, fully automated process for construction of sequence-ready barcoded libraries for 454. Genome Biol. 2010;11(2):R15.
Lizardi, et al., Mutation detection and single-molecule counting using isothermal rolling-circle amplification. *Nature Genetics*. Jul. 1998.19:(3):225-32.
Marchuk, et al. Construction of T-vectors, a rapid and general system for direct cloning of unmodified PCR products. Nucleic Acids Res. Mar. 11, 1991; 19(5): 1154.
Mardis, E. New strategies and emerging technologies for massively parallel sequencing: applications in medical research. Online Apr. 17, 2009. *Genome Med*. 2009: 1(4); 40. Available at www.ncbinlm.nih.gov/pmc/aricles/PMC2684661/?tool=pubmed. Accessed Oct. 22, 2009.
Mardis. Next-Generation DNA Sequencing Methods. The Annual Review of Genomics and Human Genetics. 2008; 9:387-402.
Meissner, et al. Reduced representation bisulfate sequencing for comparative high-resolution DNA methylation analysis. Nucleic Acids Res. Oct. 13, 2005;33(18):5868-77. Print 2005.

(56) References Cited

OTHER PUBLICATIONS

Metzker, M. Sequencing technologies—the next generation. Nat Rev Genet. Jan. 2010;11(1):31-46. Epub Dec. 8, 2009.
Meuzelaar, et al. MegaPlex PCR: a strategy for multiplex amplification. Nat Methods. Oct. 2007;4(10):835-7. Epub Sep. 16, 2007.
Meyer, et al. Parallel tagged sequencing on the 454 platform. Nat Protoc. 2008;3(2):267-78. doi: 10.1038/nprot.2007.520.
Meyer, et al. Targeted high-throughput sequencing of tagged nucleic acid samples. Nucleic Acids Res. 2007;35(15):e97.
Mitchell, et al. Circulating microRNAS as stable blood-based markers for cancer detection. Proc Natl Acad Sci U S A. Jul. 29, 2008;105(30):10513-8. Epub Jul. 28, 2008.
Mitra, et al., In situ localized amplification and contact replication of many individual DNA moecules. Nucleic Acids Research. 1999. 27:(24); e34.
Nayak, et al. Functional architecture of T7 RNA polymerase transcription complexes. *J. Mol Biol*. Aug. 10, 2007; 371(2): 490-500.
New England BioLabs Inc. NEBNext® Ultra™ Directional RNA Library Prep Kit for Illumina®. Available at https://www.neb.com/products/e7420-nebnext-ultra-directional-rna-library-prep-kit-for-illumina. Accessed Jun. 4, 2014.
Ng, et al. Targeted capture and massively parallel sequencing of 12 human exomes. *Nature*. Sep. 10, 2009. 461, 272-276. http://www.nature.com/nature/journal/v461/n7261/full/nature08250.html. Accessed Oct. 6, 2009.
Nikolaev, et al. Detection of genomic variation by selection of a 9Mb DNA region and high throughput sequencing. *PLoS One*. Aug. 17, 2009. 4(8): e6659.
Ochman, et al. Genetic applications of an inverse polymerase chain reaction. Genetics. Nov. 1988;120(3):621-3.
Office action dated Jan. 16, 2013 for U.S. Appl. No. 12/938,112.
Office action dated Feb. 5, 2014 for U.S. Appl. No. 13/750,768.
Office action dated Feb. 28, 2013 for U.S. Appl. No. 13/156,294.
Office action dated Jun. 27, 2013 for U.S. Appl. No. 12/938,112.
Office action dated Sep. 5, 2013 for U.S. Appl. No. 13/156,294.
Office action dated Oct. 9, 2013 for U.S. Appl. No. 12/938,112.
Okou, et al. Microarray-based genomic selection for high-throughput resequencing. Nat Methods. Nov. 2007;4(11):907-9. Epub Oct. 14, 2007.
Olson, M. Enrichment of super-sized resequencing targets from the human genome. Nat Methods. Nov. 2007;4(11):891-2.
Openwetware. Directional-RNAseq Prep. Available at http://openwetware.org/wiki/Directional-RNAseq_Prep. Accessed Jun. 4, 2014.
Parameswaran, et al. A pyrosequencing-tailored nucleotide barcode design unveils opportunities for large-scale sample multiplexing. Nucleic Acids Res. 2007;35(19):e130.
Pease, et al. A rapid, directional RNA-seq library preparation workflow for Illumina [reg] sequencing. Nature Methods. 2012; 9, No. 3.
Pease, et al. Rapid, directional RNA-seq library preparation kits for formalin-fixed paraffin-embedded RNA. Nature Methods. 2012; 9: Published online Sep. 27, 2012.
Pei, et al. Site-specific cleavage of duplex DNA by semisynthetic nuclease via triple-helix formation. *Pro. Natl. Acad. Sci. USA*. Dec. 1990. 87: 9858-9862.
Peng, et al. Kamchatka crab duplex-specific nuclease-mediated transcriptome subtraction method for identifying long cDNAs of differentially expressed genes. *Analytical Biochemistry*. Jan. 15, 2008. 372:2, 148-155. (abstract).
Pierce, et al. Linear-after-the-exponential polymerase chain reaction and allied technologies. Real-time detection strategies for rapid, reliable diagnosis from single cells. Methods Mol Med. 2007;132:65-85.
Porreca, et al. Multiplex amplification of large sets of human exons. Nat Methods. Nov. 2007;4(11):931-6. Epub Oct. 14, 2007.
Prashar, et al. Analysis of differential gene expression by display of 3' end restriction fragments of cDNAs. Proc Natl Acad Sci U S A. Jan. 23, 1996;93(2):659-63.
Ramsahoye, et al. Non-CpG methylation is prevalent in embryonic stem cells and may be mediated by DNA methyltransferase 3a. Proc Natl Acad Sci U S A. May 9, 2000;97(10):5237-42.
Ranasinghe, et al. Fluorescence based strategies for genetic analysis. Chem Commun (Camb). Nov. 28, 2005;(44):5487-502. Epub Sep. 30, 2005.
Riley, et al. A novel, rapid method for the isolation of terminal sequences from yeast artificial chromosome (YAC) clones. Nucleic Acids Res. May 25, 1990;18(10):2887-90.
Roberts, R. Restriction enzymes at NEB: over 30 years of innovation, the discovery, cloning and engineering of these essential reagents. *NEB Expression*. Winter. 2008. vol. 2.4. Available at www.neb.com/nebecomm/tech_reference/restriction_enzymes/feature_article_innovation.asp. Accessed Aug. 16, 2010.
Robertson. DNA methylation and human disease. Nat Rev Genet. Aug. 2005;6(8):597-610.
Roche Company. 454 life sciences, applications—sequence capture targeted region. http://www.454.com/applications/sequence-capture-targeted-region.asp. Accessed Oct. 6, 2009.
Saiki, et al. Analysis of enzymatically amplified beta-globin and HLA-DQ alpha DNA with allele-specific oligonucleotide probes. Nature. Nov. 13-19, 1986;324(6093):163-6.
Sanders, et al. Targeting individual subunits of the FokI restriction endonuclease to specific DNA strands, *Nucleic Acids Research*. Apr. 2009. *Nucleic Acids Res*. 37:(7):2105-15.
Schmid, et al. Chic and chec: genomic mapping of chromatin proteins. *Molecular Cell*. 2004. 16, No. 1, pp. 147-157. (abstract).
Stemmer, et al. Single-step assembly of a gene and entire plasmid from large numbers of oligodeoxyribonucleotides. Gene. Oct. 16, 1995;164(1):49-53.
Stephpens, et al. Automating sequence-based detection and genotyping of SNPs from diploid samples. Nat Genet. Mar. 2006;38(3):375-81. Epub Feb. 19, 2006.
Summerer, D. Enabling technologies of genomic-scale sequence enrichment for genomic-scale sequence enrichment for targeted high-throughput sequencing. *Genomics*. Dec. 2009;94(6):363-8. (*abstract*).
Summerer, et al. Microarray-based muticycle-enrichment of genomic subsets for targeted next-generation sequencing. Accepted Jun. 18, 2009. Available at www.ncbi.nlm.nih.gov/pubmed/19638418. Accessed Oct. 6, 2009.
Timblin, et al. Application for PCR technology to subtractive cDNA cloning: identification of genes expressed specifically in murine plasmacytoma cells. Nucleic Acids Res. Mar. 25, 1990;18(6):1587-93.
Tong, et al. Detection of restriction enzyme-digested target DNA by PCR amplification using a stem-loop primer: application to the detection of hypomethylated fetal DNA in maternal plasma. Clin Chem. Nov. 2007;53(11):1906-14. Epub Sep. 27, 2007.
Turner, et al. Methods for genomic partitioning. Annu Rev Genomics Hum Genet. 2009;10:263-84. doi: 10.1146/annurev-genom-082908-150112.
Varkonyi-Gasic, et al. Protocol: a highly sensitive RT-PCR method for detection and quantification of microRNAs. Plant Methods. Oct. 12, 2007;3:12.
Varley, et al. Nested Patch PCR enables highly multiplexed mutation discovery in candidate genes. Genome Res. Nov. 2008;18(11):1844-50. doi: 10.1101/gr.078204.108. Epub Oct. 10, 2008.
Vincent, et al. Helicase-dependent isothermal DNA amplification. EMBO Rep. Aug. 2004;5(8):795-800. Epub Jul. 9, 2004.
Vos, et al. AFLP: a new technique for DNA fingerprinting. Nucleic Acids Res. Nov. 11, 1995;23(21):4407-14.
Westburg. Fast, Directional RNA-Seq Library Prep. Abailable at http://www.westburg.eu/lp/rna-seq-library-preparation. Accessed on Jun. 4, 2014.
Wikipedia. ABI solid sequencing. Http://en.wikipedia.org/wild/ABI_Solid_Sequencing. Last modified Oct. 4, 2009. Accessed Oct. 22, 2009.
Wikipedia. DNA sequencing. Alailable at http://en.wikipedia.org/wiki/Next-generation_sequencing. Last modified Oct. 8, 2009. Accessed Oct. 22, 2009.

(56) References Cited

OTHER PUBLICATIONS

Young, et al. A new strategy for genome assembly using short sequence reads and reduced representation libraries. Genome Res. Feb. 2010;20(2):249-56. doi: 10.1101/gr.097956.109.
Zhang, et al. Multiplex sequencing on the Solid platform with 10, 16, or 96 barcodes. 2009 Life technologies. www3.appliedbiosystems.com/cms/groups/mcb_marketing/documents/generaldocuments/cms_065528.pdf.
Zhulidov, et al. Simple cDNA normalization using kamchatka crab duplex=specific nuclease. *Nucleic Acids Research*. Online Feb. 18, 2004. 32:3 e37.
Ziller, et al. Genomic distribution and inter-sample variation of non-CpG methylation across human cell types. PLoS Genet. Dec. 2011;7(12):e1002389. doi: 10.1371/journal.pgen.1002389. Epub Dec. 8, 2011.
Bower, et al. Targeted rapid amplification of cDNA ends (T-Race)—an improved Race reaction through degradation of non-target sequences. Nucleic Acids Res. Nov. 2010;38(21):e194. doi: 10.1093/nar/gkq816. Epub Sep. 15, 2010.
Chen, et al. BisQC: an operational pipeline for multiplexed bisulfite sequencing. BMC Genomics. Apr. 16, 2014;15:290. doi: 10.1186/1471-2164-15-290.
Chenchik, et al. Full-length cDNA cloning and determination of mRNA 5' and 3' ends by amplification of adaptor-ligated cDNA. Biotechniques. Sep. 1996;21(3):526-34.
European search report and opinion dated May 22, 2015 for EP Application No. 12842163.3.
International search report and written opinion dated Jun. 18, 2015 for PCT/US2015/018112.
U.S. Appl. No. 13/156,294, filed Jun. 8, 2011, Raymond et al.
Adamczyk, et al. Synthesis of a Chemiluminescent Acridinium Hydroxylamine (AHA) for the Direct Detection of Abasic Sites in DNA. Org. Lett. 1999; 1(5):779-781.
Adamczyk, et al. O-(Fluoresceinylmethyl) hydroxylamine (OFMHA): A Fluorescent Regent for Detection of Damaged Nucleic Acids. Bioorg. & Med. Chem. Lett. 1998; 8:3599-3602.
Ausubel, et al., Eds. Current Protocols in Molecular Biology. John Wiley & Sons, Inc. 1987 and updates.
Ballestar, et al. Methyl-CpG-binding proteins. Targeting specific gene repression. Eur J Biochem 2001; 268:1-6.
Bangs Laboratories, Inc. TechNote 205 retreived at: http:www.bangslab.com/technotes/205.pdf. Visited on Jul. 16, 2003. (8 pages).
Ben-Artzi, et al. Double-stranded RNA-dependent RNase activity associated with human immunodeficiency virus type 1 reverse transcriptase. Proc Natl Acad Sci U S A. Feb. 1, 1992;89(3):927-31.
Boturyn, et al. A simple and Sensitive Method for in Vitro Quantitation of Abasic Sites in DNA. Chem. Res. Toxicol. 1999; 12:476-482.
Boturyn, et al. Synthesis of Fluorescent Probes for the Detection of Abasic Sites in DNA. Tetrahedron. 1997; 53(15):5485-5492.
Brown, T.A. Ed. Molecular Biology, LabFax. Bios Scientific Publishers. Academic Press. 1991; pp. 147-148.
Buchman, et al. Selective RNA amplification: a novel method using dUMP-containing primers and uracil DNA glycosylase. PCR Methods Appl. Aug. 1993;3(1):28-31.
Burrows, et al. Oxidative Nucleobase Modifications Leading to Strand Scission. Chem Rev. May 7, 1998;98(3):1109-1151.
Carey, et al. Human Apurinic/Apyrimidinic Endonuclease in Processive. Biochem. 1999; 38:16553-16560.
Chan, et al. The biophysics of DNA hybridization with immobilized oligonucleotide probes. Biophys J. Dec. 1995;69(6):2243-55.
Derisi, et al. Use of cDNA microarray to analyse gene expression patterns in human cancer. Nature Genetics. 1996; 14:457-460.
Erlanger, et al. Antibodies Specific for Ribonucleosides and Ribonucleotides and Their Reaction With DNA. Proc Natl Acad Sci USA. 1964; 52:68-74.
European office action dated Apr. 1, 2011 for Application No. 03771533.1.
European search report dated Oct. 18, 2007 for Application No. 3771533.1.
European search report dated Feb. 12, 2010 for Application No. 7810169.8.
European search report dated Mar. 29, 2010 for Application No. 4815722.6.
Fodor, et al. Light-Directed, spatially addressable parallel chemical synthesis. 1991; 251: 767-773.
Freeman, et al. Fundamentals of DNA Hybridization Arrays for Gene Expression Analysis. BioTechniques. Nov. 2000; 29:1042-1044, 1046, 1048-1055.
Freshney, R.I. ed. (1987). *Animal Cell Culture*. IRL Press: Oxford, pp. vii-xii (Table of Contents Only.).
Gait, M.J., Ed. 1984 . Oligonucleotide Synthesis: A Practical Approach. IRL Press: Oxford, pp. vii-xii (Table of Contents).
Ghosh, S.S. Synthesis of 5'-Oligonucleotide Hydrazide Derivatives and Their Use in Preparation of Enzyme-Nucleic Acid Hybridization Probes. Anal. Biochem. 1989; 178:43-51.
Haraguchi, et al. Synthesis and characterization of oligodeoxynucleotides containing formamidopyrimidine lesions and nonhydrolyzable analogues. J Am Chem Soc. Apr. 3, 2002;124(13):3263-9.
Heimgartner, et al.Polyacrylic Polyhydrazides as Reagents for Detection of Glycoproteins. Anal. Biochem. 1989; 181:182-189.
Hollis, et al. Structural studies of human alkyladenine glycosylase and *E. coli* 3-methyladenine glycosylase.Mutat Res. 2000; 460(3-4):201-10.
Horn, et al. Solid supported hydrolysis of apurinic sites in synthetic oligonucleotides for rapid and efficient purification on reverse-phase cartridges. Nucl. Acids Res. 1988; 16:11559-11571.
Hottiger, et al. Strand displacement activity of the human immunodeficiency virus type 1 reverse transcriptase heterodimer and its individual subunits. J Biol Chem. Jan. 14, 1994;269(2):986-91.
Huber, et al. Processing of the primer for plus strand DNA synthesis by human immunodeficiency virus 1 reverse transcriptase. J Biol Chem. Jun. 25, 1990;265(18):10565-73.
Ide, et al. Synthesis and Damage Specificity of a Novel Probe for the Detection of Abasic Sites in DNA. Biochem. 1993; 32:8276-8283.
International Preliminary Examination Report mailed on Mar. 22, 2006 for PCT Patent Application No. PCT/US03/15825 filed May 19, 2003, 9pages.
International search report and written opinion dated Dec. 3, 2010 for PCT Application No. US10-45384.
International search report dated Jan. 2, 2008 for PCT Application No. US2007/15409.
International search report dated Jun. 14, 2005 for PCT Application No. US 2003/015825.
International search report dated Jul. 9, 2008 for PCT Application No. US2004/043710.
Karata, et al. Construction of a circular single-stranded DNA template containing a defined lesion. DNA Repair (Amst). Jul. 4, 2009;8(7):852-6.
Kawarada, et al. Antibodies Specific for Methylated DNA Elicited in Rabbits Recognize only a Single Strand Region of DNA Containing 7-Methylguanine Tohuku. J Exp Med. 1986; 149:151-161.
Khrapko, et al. A method for DNA sequencing by hybridization with oligonucleotide matrix. DNA Sequence—J. DNA Sequencing and Mapping. 1991; 1:375-388.
Kim, et al. Evidence for thiol-dependent production of oxygen radicals by 4-methyl-5-pyraziny1-3H-1,2-dithiole-3-thione (oltipraz) and 3H-1,2-dithiole-3-thione: possible relevance to the anticarcinogenic properties of 1,2-dithiole-3-thiones. Chem Res Toxicol. Mar. 1997;10(3):296-301.
Kow, et al. Detection of Abasic Sites and Oxidative DNA Base Damage Using an Elisa-like Assay. Methods. 2000; 22:164-169.
Kubo, et al. A Novel Sensitive, and Specific Assay for Abasic Sites, the Most Commonly Produced DNA Lesion. Biochem. 1992; 31:3703-3708.
Levin, et al. Comprehensive comparative analysis of strand-specific RNA sequencing methods. Nat Methods. Sep. 2010;7(9):709-15. doi: 10.1038/nmeth.1491. Epub Aug. 15, 2010.
Lhomme, et al. Abasic DNA Structure reactivity and recognition. Biopolymers. 1999; 52(2): 65-83.

(56) References Cited

OTHER PUBLICATIONS

Lindahl, T. An N-Glycosidase from *Escherichia coli* That Releases Free Uracil from DNA Containing Deaminated Cytosine Residues. Proc Natl. Acad. Sci. USA 1974; 71(9):3649-3653.
Lockhart, et al. Expression monitoring by hybridization to high-density oligonucleotide arrays. Nature Biotechnology. 1996; 14:1675-1680.
Makrigiogos, G. Fluorescent Labeling of Abasic Sites: A Novel Methodology to Detect Closely-Spaced Damage Sites in DNA. Int. J. Radiat. Biol. 1998: 74(1):99-109.
Maskos, et al. Oligonucleotide hybridisations on glass supports: a novel linker for oligonucleotide synthesis and hybridization properties of oligonucleotides synthesised in Situ. Nucl. Acids. Res. 20(7):1679-1684.
Maulik, et al. Novel Non-isotopic Detection of MutY Enzyme-recognized Mismatches in DNA Via Ultrasensitive Detection of Aldehydes. Nucl. Acids. Res. 1999: 27(5):1316-1322.
McCarthy, et al. Inducible repair of O-alkylated DNA pyrimidines in *Escherichia coli*. EMBO J. 1984; 3(3):545-50.
McHugh, et al. Novel Regents for Chemical Cleavage at Abasic Sites and UV Photoproducts in DNA. Nucl. Acids. Res. 23(10): 1664-1670.
Mitra, et al. Oxidative DNA cleavage by the antitumor antibiotic leinamycin and simple 1,2-dithiolan-3-one 1-oxides: Evidence for thiol-dependent conversion of molecular oxygen to DNA-cleaving oxygen radicals mediated by polysulfides. Journal of the American Chemical Society. 1997; vol. 119(48):11691-11692.
Mizugaki, et al. Preparation of a monoclonal antibody specific for 5-methyl-2'-deoxycytidine and its application for the detection of DNA methylation levels in human peripheral blood cells. Biol Pharm Bull. 1996; 19(12):1537-1540.
Molecular Probe Handbook Section 3.2 obtained from website at: http://www.probes.com/handbook/print/0302.html (Copyright © 1996-2003 by Molecular Probes, Inc.) Visited on Aug. 13, 2003. (18 pages).
Mullis, K.B et al., Eds. (1994). PCR: Polymerase Chain Reaction. Birkhauser: Boston, pp. xv-xvii (Table of Contents).
Nakamura, et al. Highly Sensitive Apurinic/Apyrimidinic site Assay Can Detect Spontaneous and Chemically Induced Depurination Under Physiological Conditions. Cancer Res. 1998; 58:222-225.
Nedderman, et al. Cloning and expression of human G/T mismatch-specific thymine-DNA glycosylase. J Biol Chem. 1996; 271(22):12767-74.
Nugen, Inc. Ovation Biotin RNA Amplification and Labeling System User Guite. Catalog #2300-12. Published 2004.
Nugen, Inc. Technical Report #1. The Ovation Biotin System Validation for Use with Affymetrix GeneChip Arrays. Published 2004.
O'Shannessy, et al. Immobilization of Glycoconjugates by Their Oligosaccharides: Use of Hydrazido-Derivatized Matrices. Anal. Biochem. 1990; 191:1-8.
Office action dated Feb. 8, 2012 for EP Application No. 07810169.8.
Office action dated Feb. 17, 2011 for U.S. Appl. No. 12/305,633.
Office action dated Mar. 1, 2010 for U.S. Appl. No. 10/441,663.
Office action dated Mar. 7, 2007 for U.S. Appl. No. 10/441,663.
Office action dated May 16, 2011 for U.S. Appl. No. 11/948,784.
Office action dated May 25, 2006 for U.S. Appl. No. 10/441,663.
Office action dated Jun. 6, 2012 for U.S. Appl. No. 10/441,663.
Office action dated Jul. 5, 2007 for U.S. Appl. No. 10/441,663.
Office action dated Jul. 8, 2009 for U.S. Appl. No. 10/441,663.
Office action dated Jul. 15, 2008 for U.S. Appl. No. 10/441,663.
Office action dated Aug. 18, 2010 for U.S. Appl. No. 12/305,633.
Office action dated Sep. 9, 2010 for U.S. Appl. No. 10/441,663.
Office action dated Sep. 18, 2006 for U.S. Appl. No. 10/441,663.
Office action dated Sep. 24, 2009 for U.S. Appl. No. 10/441,663.
Office action dated Oct. 14, 2010 for U.S. Appl. No. 11/948,784.
Office action dated Nov. 7, 2012 for U.S. Appl. No. 13/411,170.
Office action dated Nov. 13, 2012 for U.S. Appl. No. 12/855,611.
Office action dated Dec. 5, 2008 for U.S. Appl. No. 10/441,663.
Office action dated Dec. 17, 2007 for U.S. Appl. No. 10/441,663.
Pang, et al. Use of modified nucleotides and uracil-DNA glycosylase (UNG) for the control of contamination in the PCR-based amplification of RNA. Molecular and Cellular Probes. 1992; 6:251-256.
Parkhomchuk, et al. Transcriptome analysis by strand-specific sequencing of complementary DNA. Nucleic Acids Res. Oct. 2009;37(18):e123.
Pease, et al. Light-generated oligonucleotide arrays for rapid DNA sequence analysis. Proc. Natl. Acad. Sci. USA 1994; 91:5022-5026.
Pollack, et al. Genome-wide analysis of DNA copy-number changes using cDNA microarrays. Nature Genet. 1999; 23:41-46.
Proudnikov, et al. Chemical methods of DNA and RNA fluorescent labeling. Nucleic Acids Res. Nov. 15, 1996;24(22):4535-42.
Sambrook, J. et al., Eds. (1989). *Molecular Cloning: A Laboratory Manual*. 2nd Edition, Cold Spring Harbor Laboratory Press, pp. xi-xxxviii (Table of Contents).
Sano, et al. Detection of heavy methylation in human repetitive DNA subsets by a monoclonal antibody against 5-methylcytosine. Biochim Biophys Acta. 1988; 951(1):157-65.
Sartori, et al. A novel uracil-DNA glycosylase with broad substrate specificity and an unusual active site. EMBO J. 2002; 21(12):3182-91.
Schena, et al. Parallel human genome analysis: microarray-based espression monitoring of 1000 genes. Proc Natl. Acad. Sci. USA Biochemistry. 1996; 93:10614-10619.
Schena, et al. Quantitative monitoring of gene expression patterns with a complementary DNA microarray. Science. 1995; 270:467-470.
Shalon, et al. Parallel human genome analysis: microarray system for analyzing complex DNA samples using two-color fluorescent probe hybridization. Genome Res. 1996; 6:639-645.
Shida, et al. Cleavage of Single-and double-Stranded DNAs Containing an Abasic Residue by *Escherichia coli* Exonuclease III (AP Endonuclease VI) Nucl. Acids. Res. 1996; 24(22):4572-4576.
Sluppahaug, et al. Low incorporation of dUMP by some thermostable DNA polymerases may limit their use in PCR amplifications. Anal. Biochem. 1993; 211:164-169.
Sohail, et al. Human activation-induced cytidine deaminase causes transcription-dependent, strand-biased C to U deaminations. Nucleic Acids Res. 2003; 31(12):2990-4.
Srivastava, et al. Mammalian Abasic Site Base Excision Repair. Identification of the Reaction Sequence and Rate-Determining Steps. J. Biol. Chem. 1998; 273(33):21203-21209.
Steullet, et al. Clevage of Abasic Sites in DNA by Intercalator-amines. Bioorganic and Medicinal Chem. 1999; 7:2531-2540.
Stratagene catalog, Gene Characterizatin Kits. 1988 p. 39.
Sugiyama, et al. Chemistry of thermal degradation of abasic sites in DNA. Mechanistic investigation on thermal DNA stand clevage of alkylated DNA. Chem. Res. Toxicol. 1994; 1:673-683.
Vairapandi, et al. Partial purification and characterization of human 5- methylcytosine-DNA glycosylase. Oncogene. 1996; 13(5):933-8.
Vairapandi, et al. Human DNA-demethylating activity: a glycosylase associated with RNA and PCNA. J Cell Biochem. 2000; 79(2):249-60.
Wilchek, et al. Labeling Glycoconjugates with Hydrazide Reagents. Methods Enzymol. 1987; 138:429-442.
Wolffe, et al. DNA demethylation. Proc Natl Acad Sci USA. 1999; 96(11):5894-6.
Zalipsky, S. Functionalized Poly(ethylene glycol) for Preparation of Biologically Relevant Congugates. Bioconjugate Chem. 1995; 6:150-165.
Zang, et al. DNA alkylation by leinamycin can be triggered by cyanide and phosphines. Bioorg Med Chem Left. Jun. 18, 2001;11(12):1511-5.
Zhu, et al. Overexpression of 5-methylcytosine DNA glycosylase in human embryonic kidney cells EcR293 demethylates the promoter of a hormone-regulated reporter gene. Proc Natl Acad Sci USA. 2001; 98(9):5031-6.
Zhu, et al. 5-Methylcytosine DNA glycosylase activity is also present in the human MBD4 (G/T mismatch glycosylase) and in a related avian sequence. Nucleic Acids Res. 2000; 28(21):4157-65.
Alvarado, et al. Multiplexed direct genomic selection (MDiGS): a pooled BAC capture approach for highly accurate CNV and SNP/

(56) References Cited

OTHER PUBLICATIONS

INDEL detection. Nucleic Acids Res. Jun. 2014;42(10):e82. doi: 10.1093/nar/gku218. Epub Mar. 20, 2014.
CNV detection by ion semiconductor sequencing. Life Technologies. 2014.
McClure, et al. Bovine exome sequence analysis and targeted SNP genotyping of recessive fertility defects BH1, HH2, and HH3 reveal a putative causative mutation in SMC2 for HH3. PLoS One. Mar. 25, 2014;9(3):e92769. doi: 10.1371/journal.pone.0092769. eCollection 2014.
Pabinger, et al. A survey of tools for variant analysis of next-generation genome sequencing data. Brief Bioinform. Mar. 2014;15(2):256-78. doi: 10.1093/bib/bbs086. Epub Jan. 21, 2013.
Singapore exam report dated Apr. 7, 2015 for SG Application No. 11201404243W.
Office action dated Jun. 30, 2008 for U.S. Appl. No. 11/026,280.
Office action dated Apr. 3, 2015 for CN Application No. 2012800608251.
Archer, et al. Selective and flexible depletion of problematic sequences from RNA-seq libraries at the cDNA stage. BMC Genomics. May 26, 2014;15:401. doi: 10.1186/1471-2164-15-401.
International search report and written opinion dated Jul. 15, 2014 for PCT Application No. US2014/028356.
International search report and written opinion dated Jul. 29, 2014 for PCT Application No. US2014/24581.
U.S. Appl. No. 14/012,409, filed Aug. 28, 2013, Kurn et al.
Combined search and examination report dated Apr. 24, 2013 for GB1305340.
European search report and search opinion dated Apr. 3, 2013 for Application No. 10808789.1.
Neylon, et al. Chemical and biochemical strategies for the randomization of protein encoding DNA sequences: library construction methods for directed evolution. Nucleic Acids Res. Feb. 27, 2004;32(4):1448-59. Print 2004.
Office action dated Jun. 19, 2013 for U.S. Appl. No. 12/855,611.
Xiao, et al. Sequential amplification of flanking sequences by Y-shaped adaptor dependent extension using multiple templates. Zhi Wu Sheng Li Yu Fen Zi Sheng Wu Xue Xue Bao (Journal of Plant Physiology and Molecular Biology). Feb. 2007;33(1):85-90.
Zheng, et al. Titration-free 454 sequencing using Y adapters. Nat Protoc. Aug. 18, 2011;6(9):1367-76. doi: 10.1038/nprot.2011.369.
Office action dated Jul. 9, 2015 for U.S. Appl. No. 14/211,261.
Office action dated Jul. 15, 2015 for U.S. Appl. No. 13/750,768.
Office action dated Jul. 15, 2015 for U.S. Appl. No. 13/938,059.
Shendure, et al. Accurate multiplex polony sequencing of an evolved bacterial genome. Science. Sep. 9, 2005;309(5741):1728-32. Epub Aug. 4, 2005.
Shendure, et al. Accurate multiplex polony sequencing of an evolved bacterial genome. Science. Sep. 9, 2005;309(5741):1728-32. Epub Aug. 4, 2005. Supplemental Materials. 41 pages.

Figure 1. Conventional system: Strand marking of cDNA inserts is not sufficient for directional library construction.
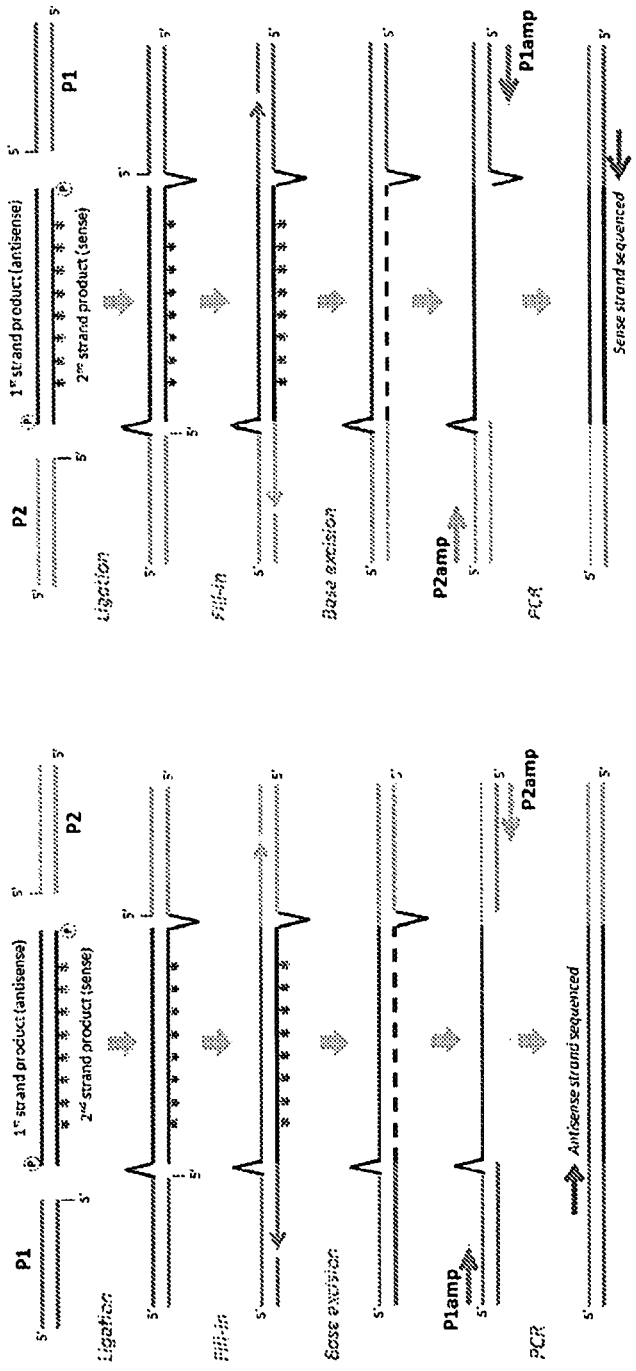
The asterisks in the diagram (*) indicate dUTP incorporation.

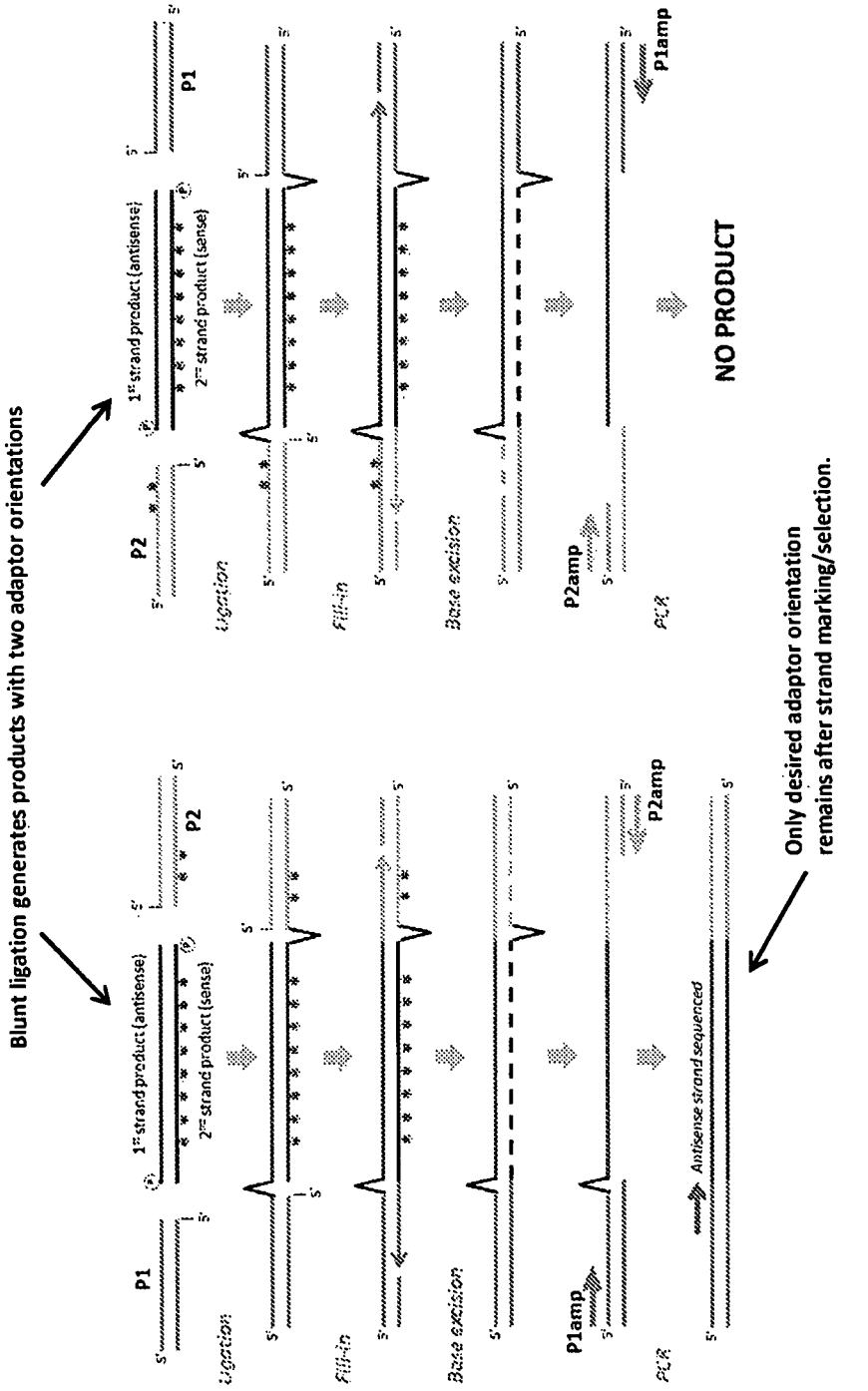
Figure 2. Construction of directional (strand-specific) cDNA libraries using duplex adaptors: Strand marking of both cDNA and one adaptor results in directional library construction.

Figure 3. Summary of strand retention efficiency data for sequence reads mapping to coding exons of human mRNAs.

| Library modifications | | | | % of all reads | | | % of reads mapping to coding exons | |
|---|---|---|---|---|---|---|---|---|
| bases used in 2ss reaction | bases used in P2 adaptor | base excision | total reads | mapped | not mapped | strand orientation expected | strand orientation observed - sense* | strand orientation observed - antisense* |
| dA,dC,cG,dT | dA,dC,cG,dT | none | 3261009 | 89.8 | 10.2 | sense and antisense | 52.3 | 47.7 |
| dA,dC,cG,dT | dA,dC,cG,dT | UNG+APE | 4111334 | 89.1 | 10.9 | sense and antisense | 51.1 | 48.9 |
| dA,dC,cG,dU | dA,dC,cG,dU | UNG+APE | 4829979 | 93.8 | 6.2 | antisense only | 2.1 | 97.9 |
| dA,dC,cG,dT | dA,dC,cG,dT | none | 3673934 | 89.6 | 10.4 | sense and antisense | 52.5 | 47.5 |
| dA,dC,cG,dT | dA,dC,cG,dT | UNG+DMED | 3977383 | 89.2 | 10.8 | sense and antisense | 51.2 | 48.8 |
| dA,dC,cG,dU | dA,dC,cG,dU | UNG+DMED | 4616560 | 93.8 | 6.2 | antisense only | 1.9 | 98.1 |

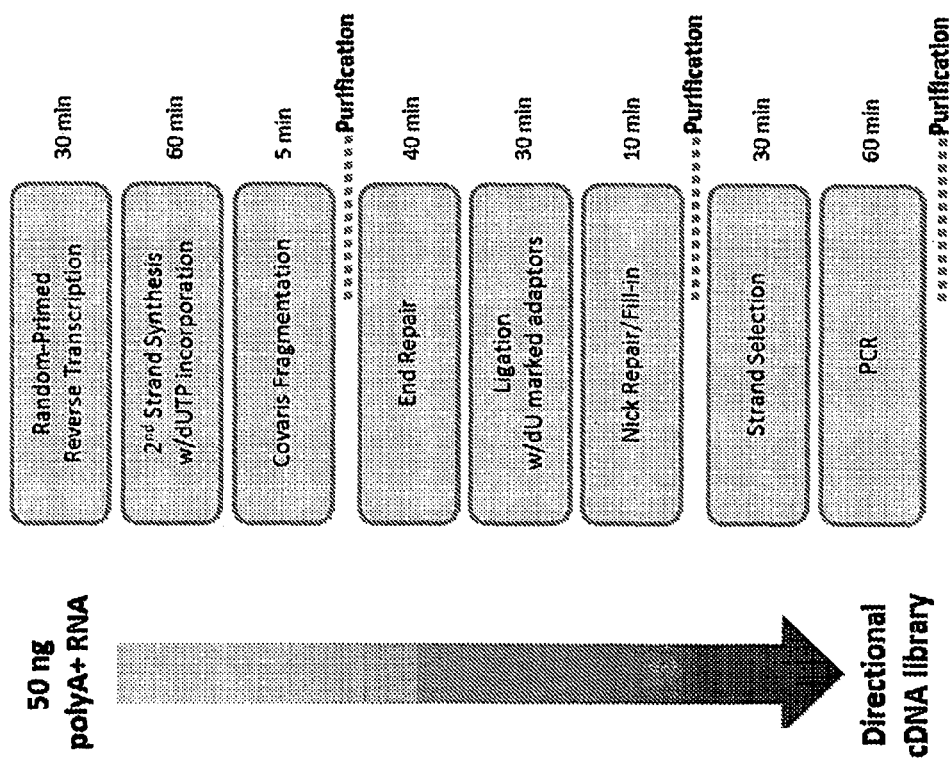
Figure 4. End-to-end workflow for construction of a directional cDNA library.

COMPOSITIONS AND METHODS FOR DIRECTIONAL NUCLEIC ACID AMPLIFICATION AND SEQUENCING

CROSS-REFERENCE

This application is a National Stage of International Application Number PCT/US2012/061218, filed Oct. 19, 2012, which claims the benefit of U.S. Provisional Application No. 61/549,162, filed Oct. 19, 2011, which application is incorporated herein by reference.

BACKGROUND OF THE INVENTION

Recent advances in high-throughput, next generation sequencing technologies have enabled whole genome sequencing and new approaches to functional genomics, including comprehensive analysis of any transcriptome. One of these next generation sequencing methods involves direct sequencing of complementary DNA (cDNA) generated from messenger and structural RNAs (RNA-Seq). RNA-Seq provides several key advantages over traditional sequencing methods. First, it allows for high resolution study of all expressed transcripts, annotating the 5' and 3' ends and splice junctions of each transcript. Second, RNA-Seq allows for quantification of the relative number of transcripts in each cell. Third, RNA-Seq provides a way to measure and characterize RNA splicing by measuring the levels of each splice variant. Together, these advancements have provided new insights into individual cell function.

One drawback of performing standard RNA-Seq is the lack of information on the direction of transcription. Standard cDNA libraries constructed for RNA-Seq consist of randomly primed double-stranded cDNA. Non-directional ligation of adaptors containing universal priming sites prior to sequencing leads to a loss of information as to which strand was present in the original RNA template. Although strand information can be inferred in some cases by subsequent analysis, for example, by using open reading frame (ORF) information in transcripts that encode for a protein, or by assessing splice site information in eukaryotic genomes, direct information on the originating strand is highly desirable. For example, direct information on which strand was present in the original RNA sample is needed to assign the sense strand to a non-coding RNA, and when resolving overlapping transcripts.

Several methods have recently been developed for strand-specific RNA-Seq. These methods can be divided into two main classes. The first class utilizes distinct adaptors in a known orientation relative to the 5' and 3' end of the RNA transcript. The end result is a cDNA library where the 5' and 3' end of the original RNA are flanked by two distinct adaptors. A disadvantage of this method is that only the ends of the cloned molecules preserve directional information. This can be problematic for strand-specific manipulations of long clones, and can lead to loss of directional information when there is fragmentation.

The second class of strand-specific RNA-Seq methods marks one strand of either the original RNA (for example, by bisulfate treatment) or the transcribed cDNA (for example, by incorporation of modified nucleotides), followed by degradation of the unmarked strand. Strand marking by bisulfite treatment of RNA is labor intensive and requires alignment of the sequencing reads to reference genomes that have all the cytosine bases converted to thymines on one of the two strands. The analysis is further complicated due to the fact that base conversion efficiency during bisulfite treatment is imperfect, i.e. less than 100%.

Strand marking by modification of the second strand of cDNA has become the preferred approach for directional cDNA cloning and sequencing (Levin et al., 2010). However, cDNA second strand marking approaches, such as the one described in WO 2011/003630, are not sufficient to preserve directionality information when using conventional blunt-end ligation and cDNA library construction strategies with duplex adaptors, where two universal sequencing sites are introduced by two separate adaptors. The marking approach described in WO 2011/000360 utilizes a four-step process, consisting of 1) incorporation of a cleavable nucleotide into one strand of the cDNA insert, 2) end repair of the cDNA insert, 3) non-directional ligation of adaptors containing universal sequencing sites and 4) selective hydrolysis of library fragments with undesired adaptor orientation. To preserve directionality information, the method requires that the 5' and 3' ends of the strand selected for amplification are marked differentially, which can be achieved, for example, by ligation of directional (i.e. polarity-specific) adaptors, or by use of a specialized forked adaptor where each strand of a double-stranded polynucleotide is covalently attached to two distinct universal sequencing sites, one sequencing site at each end of the strand. Application of the methodology described in WO 2011/000360 does not result in directional sequencing libraries when using conventional duplex adaptors because the marked strand, i.e. the strand with incorporated cleavable nucleotides, is not differentially labeled at its 5' and 3' ends.

There is a need for improved methods for directional cDNA sequencing from cDNA libraries constructed with conventional duplex adaptors. The invention described herein fulfills this need.

SUMMARY OF THE INVENTION

The present invention provides novel methods, compositions, and kits for construction of directional cDNA libraries and directional cDNA sequencing. Specifically, an important aspect of this invention is the methods and compositions that allow for directional cDNA cloning and strand retention using duplex adaptors and blunt-end ligation, thereby generating ligation products with two adaptor orientations. In one aspect, the invention provides a method for cloning cDNA while retaining the directionality and strand information of the original RNA sample. In some embodiments, the method comprises: a) reverse transcribing a RNA sample to generate a first strand cDNA; b) generating a second strand cDNA from the first strand cDNA, wherein at least one of the four dNTPs dATP, dCTP, dGTP or dTTP is replaced by a modified dNTP during second strand synthesis and incorporated into the second strand, thereby generating a double-stranded cDNA; c) performing end repair on the double-stranded cDNA; d) ligating adaptors to the double-stranded cDNA, wherein only one of the adaptors has the modified dNTP incorporated into a ligation strand of the adaptor; e) performing gap repair; and f) selectively cleaving the second strand and the ligation strand of the adaptor that has the modified dNTP by a suitable cleavage agent, thereby generating a directional cDNA library comprising the first strand cDNA In a further aspect, the method optionally comprises fragmenting the double stranded cDNA prior to performing end repair on the double-stranded cDNA. In a specific embodiment, the method further comprises amplifying the remaining cDNA strand or the cDNA strand that does not comprise the modified nucleotide, thereby generating amplified products. In another specific embodiment, the method further comprises sequencing the remaining cDNA strand or the amplified products.

In another aspect, the invention provides for a method for selective removal of cDNA constructs in the undesired orientation.

In yet another aspect, the invention provides a method for whole transcriptome directional sequencing, comprising: a) reverse transcribing a RNA sample to generate a first strand cDNA; b) generating a second strand cDNA from the first strand cDNA, wherein at least one of the four dNTPs dATP, dCTP, dGTP or dTTP is replaced by a modified dNTP during second strand synthesis and incorporated into the second strand, thereby generating a double-stranded cDNA; c) performing end repair on the double-stranded cDNA; d) ligating adaptors to the double-stranded cDNA, wherein only one of the adaptors has the modified dNTP incorporated into a ligation strand of the adaptor; e) performing gap repair; f) selectively cleaving the second strand and the ligation strand of the adaptor that has the modified dNTP by a suitable cleavage agent, thereby generating a directional cDNA library comprising the first strand cDNA and h) amplification and/or sequencing of the directional cDNA library. In a further aspect, the method optionally comprises fragmenting the double stranded cDNA prior to performing end repair on the double-stranded cDNA.

In one aspect of any one of the foregoing aspects, the present invention provides for cleaving a base portion of the modified nucleotide thereby forming an abasic site. In a preferred embodiment, the modified nucleotide comprises dUTP. In some cases the cleavage agent comprises a glycosylase. In a preferred embodiment, the glycosylase comprises UNG. In some cases, the cleavage agent comprises a glycosylase and an endonuclease. In some cases, the endonuclease comprises an apurinic/apyrimidinic endonuclease (APE). In some cases, the cleavage agent comprises a glycosylase and a APE. In some cases, the cleavage agent comprises a UNG and a APE. In some cases, the cleavage agent comprises a glycosylase and a polyamine. In a preferred embodiment, the polyamine is N,N-dimethylethylenediamine (DMED). In some cases, the cleavage agent comprises a glycosylase and DMED. In some cases, the cleavage agent comprises a UNG and DMED.

In another aspect of any one of the foregoing aspects, the method further comprises creating nicks in a phosphodiester backbone at an abasic site with an enzyme, chemical agent, and/or heat following removal of a base portion of the modified nucleotide. In some cases, cleaving a phosphodiester backbone at an abasic site following removal of a base portion of the modified nucleotide comprises using an enzyme. In a preferred embodiment, the enzyme is an endonuclease. In some cases, the endonuclease comprises an apurinic/apyrimidinic endonuclease (APE). In some cases, creating nicks at an abasic site following removal of a base portion of the modified nucleotide comprises using a chemical agent. In some cases, the chemical agent comprises a primary amine or a polyamine. In a preferred embodiment, the polyamine is N,N-dimethylethylenediamine (DMED).

In another aspect of any of the foregoing aspects, the method further comprises cleaving the RNA sample following reverse transcription of the RNA sample. In some cases, cleaving the RNA sample comprises exposing the RNA sample to an RNase. In a preferred embodiment, the RNase is RNase H. In some cases, cleaving the RNA sample comprises exposing the RNA sample to heat or chemical treatment or a combination thereof.

In another aspect of any of the foregoing aspects, the method further comprises reducing or depleting non-desired nucleic acid sequences. In some cases, the non-desired nucleic acid is ribosomal RNA (rRNA).

In another aspect of any of the foregoing aspects, the amplification of the remaining cDNA strand comprises polymerase chain reaction (PCR), strand displacement amplification (SDA), multiple displacement amplification (MDA), rolling circle amplification (RCA), single primer isothermal amplification (SPIA), or ligase chain reaction (LCR). In some cases, the amplification comprises PCR. In some case, the amplification comprises SPIA.

In another aspect of any of the foregoing aspects, the sequencing of the remaining cDNA strand or amplified products from the remaining cDNA strand comprises next generation sequencing.

Kits for performing any of the methods described herein are another feature of the invention. Such kits may include reagents, enzymes and platforms for amplification, cloning and sequencing of nucleic acids. In one embodiment, a kit is provided comprising: a) one or more primers; b) a reverse transcription enzyme, c) a glycosylase and d) an adaptor or several adaptors wherein one of the adaptors comprises at least one modified nucleotide in a ligation strand of said adaptor. In another embodiment, the kit further comprises reagents for amplification. In another embodiment, the kit further comprises a polyamine, an APE, or a combination thereof. In another embodiment, the kit further comprises at least one modified nucleotide or dNTP. In some cases, the modified nucleotide comprises dUTP. In some cases, the glycosylase comprises UNG. In yet another embodiment, the kit further comprises reagents for sequencing. A kit will preferably include instructions for employing the kit components as well as the use of any other reagent not included in the kit.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following description that sets forth illustrative embodiments, in which the principles of the invention are utilized, and the accompanying drawings of which:

FIG. 1 depicts construction of a non-directional cDNA library with conventional duplex adaptors (i.e. where ligation products have two adaptor orientations) and strand marking.

FIG. 2 depicts construction of directional (strand-specific) cDNA libraries with conventional duplex adaptors using the methods of the invention.

FIG. 3 depicts a table summarizing strand retention efficiency data using the methods of the invention.

FIG. 4 depicts a flow diagram illustrating the steps for generating a directional cDNA library using the methods of the invention.

DETAILED DESCRIPTION OF THE INVENTION

General

Reference will now be made in detail to exemplary embodiments of the invention. While the disclosed methods and compositions will be described in conjunction with the exemplary embodiments, it will be understood that these exemplary embodiments are not intended to limit the invention. On the contrary, the invention is intended to encompass alternatives, modifications and equivalents, which may be included in the spirit and scope of the invention.

In one embodiment, the present invention provides methods and compositions for construction of directional cDNA libraries. The methods described herein enable directional cDNA cloning and strand retention using conventional duplex adaptors and blunt-end ligation. The methods further enable generation of strand-specific cDNA which can be further amplified using a variety of amplification methods. In another embodiment, the present invention provides methods for whole transcriptome directional sequencing. In yet another embodiment, the present invention provides methods and compositions for generation of a directional, rRNA-depleted cDNA library.

One aspect involves a method for generation of a directional cDNA library. The first step in the method entails use of an RNA sample or RNA template from which a first strand cDNA can be generated through reverse transcription. The RNA sample can be derived from any number of sources known in the art including, but not limited to, messenger RNA (mRNA) or ribosomal RNA (rRNA) in either purified or unpurified forms and reverse transcription can be performed using any number of RNA dependent DNA polymerases known in the art. In one embodiment, the RNA template can be derived from DNA including, but not limited to, genomic DNA wherein the DNA is converted to RNA using methods known in the art including, but not limited to, transcription. In a preferred embodiment, as exemplified in FIG. 4, the RNA can be poly A+RNA. Reverse transcription of the RNA sample can be performed using primers comprising sequence complementary to known sequences or comprising random sequences. In one embodiment, the primers used in the methods described herein can be composite primers comprising both DNA and RNA. In a preferred embodiment, the RNA sample can be reverse transcribed using random hexamer primers.

The second step in the method described herein for the generation of a directional cDNA library entails generating a second strand cDNA from the first strand cDNA in order to form a double stranded cDNA. Second strand synthesis can be performed in the presence of a modified dNTP. In a preferred embodiment, second strand synthesis can be performed in the presence of dATP, dCTP, dGTP and dUTP in place of dTTP. Second strand synthesis in the presence of dUTP causes incorporation of at least one dUTP in the strand of the second strand cDNA. The dUTP in the second strand cDNA serves to mark the second strand since in this context dUTP is a modified or non-canonical dNTP. Second strand synthesis can be performed using any number of second strand synthesis protocols known in the art including, but not limited to, those that utilize RNase H mediated nick translation in combination with a DNA dependent DNA polymerase such as DNA polymerase I (not Klenow Fragment). Second strand synthesis can also be performed using commercially available kits such as New England Biolabs NEBNext Second Strand Synthesis Module The second strand cDNA product produced during second strand synthesis can also be referred to as the sense strand product since the sequence of the second strand cDNA comprises the sequence found in the template RNA, while the first strand cDNA can be also be referred to as the antisense strand product. In another embodiment, second strand synthesis can be performed following removal of the RNA template after first strand synthesis. Removal of the RNA template can be achieved using enzymes, heat denaturation, or chemical denaturation. Enzymatic mediated removal of the RNA template can be performed with an RNase, preferably RNase H, or a combination of enzymes, such as RNase H and RNase1 As a further aspect to this embodiment, second strand synthesis can be performed using a primer comprising sequence that is complementary to sequence present in the first strand product in conjunction with the use of a DNA dependent DNA polymerase.

In one embodiment, second strand synthesis can be followed by end repair of the double stranded cDNA generated following second strand synthesis. End repair can include the generation of blunt ends, non-blunt ends (i.e sticky or cohesive ends), or single base overhangs such as the addition of a single dA nucleotide to the 3'-end of the double-stranded DNA product, by a polymerase lacking 3'-exonuclease activity. In a preferred embodiment, end repair can be performed on the double stranded cDNA to produce blunt ends wherein the double stranded cDNA contains 5' phosphates and 3' hydroxyls. End repair can be performed using any number of enzymes and/or methods known in the art including, but not limited to, commercially available kits such as the Encore™ Ultra Low Input NGS Library System I.

In one embodiment, end repair can be performed after the double-stranded cDNA has been fragmented. Fragmentation of the double-stranded products can be achieved through methods known in the art. Fragmentation can be through physical fragmentation methods and/or enzymatic fragmentation methods. Physical fragmentation methods can include nebulization, sonication, and/or hydrodynamic shearing. In a preferred embodiment, the fragmentation of the double-stranded cDNA is performed by sonication. Reagents for carrying out enzymatic fragmentation reactions are commercially available (e.g, from New England Biolabs).

Following end repair of the double stranded cDNA, the methods described herein for generating directional cDNA libraries involve ligating adaptors to the double-stranded cDNA. The adaptors can be any type of adaptor known in the art including, but not limited to, conventional duplex or double stranded adaptors. In a preferred embodiment, the adaptors can be double stranded DNA adaptors. In an embodiment, the adaptors can be oligonucleotides of known sequence and, thus, allow generation and/or use of sequence specific primers for amplification and/or sequencing of any polynucleotides to which the adaptor(s) is appended or attached. Preferably, the adaptors can be any adaptors that can be marked and selected for by methods known in the art. In a preferred embodiment, the adaptors can be marked via incorporation of at least one modified dNTP. In a preferred embodiment, one and only one of the adaptors comprises a modified dNTP while the other or any other adaptor(s) does not comprise the modified dNTP. In a preferred embodiment one and only one of the adaptors comprises a modified dNTP in a ligation strand of said adaptor, while the other or any other adaptor(s) does not comprise the modified dNTP in a ligation strand of said adaptor(s). In one embodiment, the modified dNTP is dUTP. In a preferred embodiment, the adaptors can be appended to the double-stranded product in multiple orientations. In a preferred embodiment, the methods described herein can involve the use of two conventional duplex adaptors comprising double stranded DNA of known sequence that are blunt ended and can bind to the double stranded product in one of two orientations, wherein one of the adaptors comprises a modified dNTP incorporated into the ligation strand while the other adaptor does not contain the modified dNTP in the ligation strand. In a preferred embodiment, the modified dNTP is dUTP.

According to the methods described herein, the adaptors can be ligated to the double-stranded cDNA by blunt end ligation in either of two orientations. One of the adaptors comprises a modified dNTP (preferably dUTP) incorporated into the ligation strand while the other adaptor does not comprise the modified dNTP (preferably dUTP) incorporated into the ligation strand. In one embodiment, the ligation of the adaptors to the double stranded cDNA creates a gap between the non-ligation strand of either of the adaptors and a strand of the double-stranded cDNA, whereby the non-ligation strand of the respective adaptor is not bound to a strand of the double stranded cDNA. As such, a gap repair or fill-in reaction can be performed using any number of methods known in the art including, but not limited to, the use of a DNA dependent DNA polymerase with weak or no strand displacement activity.

Following ligation of the adaptors and, optionally, gap repair, a double stranded cDNA/adaptor complex is generated. The complex can then be subjected to strand selection. Strand selection can entail base excision of the modified dNTP that is incorporated into the second strand of the double stranded cDNA and the ligation strand of one and only one of the adaptors ligated to the double stranded cDNA. Base excision of the modified dNTP can be performed using an enzyme, chemical agent, and/or heat and creates an abasic site wherever the modified dNTP is incorporated in a nucleotide sequence. In addition to base excision, the methods of the present invention can also entail cleavage of the phoshodiester bond at the abasic site. The phosphodiester bond can also be referred to as the phosphodiester backbone or DNA backbone. Cleavage of the DNA backbone can be performed using any number of agents including an enzyme, chemical agent, heat, or any combination thereof.

Base excision and/or cleavage of the DNA backbone leads to the cleavage or removal of the marked second strand that comprises a modified dNTP as well as the ligation strand of the one adaptor that comprises the modified dNTP, while the unmarked strand and the ligation strand of the adaptor that does not contain the modified dNTP remain intact. In this instance, the remaining strand of the double strand cDNA following base excision and/or DNA backbone cleavage is the first strand cDNA or the antisense strand product. In addition, base excision and/or DNA backbone cleavage also cleaves or removes the ligation strand of the one adaptor that comprises the modified dNTP, regardless of which strand of the double stranded cDNA said ligation strand is ligated to. Amplification of the remaining strand can be preferentially performed using a primer whose sequence is complementary to the ligation strand of the adaptor that does not comprise the modified dNTP. Amplification using a primer whose sequence is complementary to the ligation strand of the adaptor that comprises the modified dNTP produces no product since that ligation strand has been cleaved and/or removed following base excision and/or cleavage of the modified dNTP. Amplification of the remaining strand can be performed using any number of amplification techniques known in the art including, but not limited to, polymerase chain reaction (PCR). Following amplification of the remaining strand, sequencing of the amplified products can be performed using primers complementary to sequences present in the ligation strand of the adaptor that does not comprise the modified dNTP, which ensures sequencing of only the unmarked first strand cDNA or the antisense strand product that remained after strand selection. Sequencing can be performed on the remaining cDNA directly and/or on the products resulting from amplification of the remaining strand.

Sequencing can be performed using any of sequencing methods known in the art including, but not limited to, next generation sequencing methods. The methods of the present invention as described above result in the generation of directional cDNA libraries that comprises cDNAs of the antisense orientation or first strand cDNA due to the marking and cleavage or removal of the sense strand product (second strand cDNA).

In another embodiment, the cleaved or degraded marked strands can be removed prior to amplification and/or sequencing of the remaining strand. In a preferred embodiment, the cleaved second strand and cleaved ligation strand of the one adaptor that comprises the modified dNTP can be removed prior to amplification and/or sequencing of the remaining first strand cDNA or antisense product. In yet another preferred embodiment, the remaining first strand cDNA (antisense product) can be purified prior to amplification and/or sequencing. Purification of the remaining strand can be performed using methods known in the art for purification of cDNA such as kits commercially available from Qiagen and/or Roche.

In an alternative embodiment, the methods described herein can be used to generate a directional cDNA library that comprises cDNAs in the sense orientation or second strand cDNA. In this embodiment, the methods described herein can be performed as described above with the exceptions that the first strand synthesis from the RNA template, as opposed to the second strand synthesis as described above, can be performed in the presence of a modified dNTP, and second strand synthesis is performed in the presence of unmodified dNTPs or classic dNTPs. In one aspect of this embodiment, the dNTPs including any and all modified dNTPs used during first strand synthesis can be removed, washed away, or replaced with unmodified dNTPs prior to second strand synthesis. As a further aspect of this embodiment, unmodified dNTPs can be used during second strand synthesis. In a preferred embodiment, the modified dNTP comprises dUTP. The antisense strand product (first strand cDNA) marked with a modified dNTP and ligated to the one and only one adaptor that comprises the modified dNTP in the ligation strand of said adaptor can be selectively cleaved or removed. As such, the remaining strand and ligated adaptor available for downstream amplification and/or sequencing comprises the sense strand product ligated to the adaptor that does not comprise the modified dNTP in the ligation strand of said adaptor.

A schematic of a preferred embodiment of the methods described herein for generating and sequencing a directional strand specific cDNA.library is illustrated in FIG. 2. Overall, the method illustrated in FIG. 2 allows determination of the strand orientation of a template RNA used to generate cDNA with improved efficiency over conventional methods as illustrated in FIG. 1. The methods illustrated in FIGS. 1 and 2 both use strand marking of the cDNA and blunt end ligation of conventional duplex adaptors to the cDNA generated from template RNA as means for determining strand orientation. In both FIGS. 1 and 2, the method involves blunt end ligating double-stranded duplex adaptors (P1/P2 in FIGS. 1 and 2) to a double stranded cDNA complex formed from an RNA sample wherein the second strand product, which is also referred to as the sense strand product since it is complementary to and of the same strand orientation as the RNA template, is marked via incorporation of dUTP during second strand synthesis. In a preferred embodiment as illustrated in both FIGS. 1 and 2, the duplex adaptors do not contain free 5' phosphate groups. As such, both adaptors (P1/P2) contain a strand (the ligation strand) that ligates with the free 5' phosphate on the double-stranded cDNA and a strand that does not ligate (non-ligation strand) to the double-stranded cDNA. Ligation can be facilitated through the use of enzymes (i.e. T4 DNA ligase) and methods known in the art, including, but not limited to, commercially available kits such as the Encore™ Ultra Low Input NGS Library System. In a preferred embodiment of the present invention as depicted in FIG. 2, the ligation strand of one and only one of the adaptors (P2) is marked via incorporation of dUTP. As depicted in FIGS. 1 and 2, ligation of the duplex adaptors can occur in one of two orientations. In the schematic on the left side of FIGS. 1 and 2, the ligation strand of the P2 adaptor is ligated to the marked sense strand (second strand product). In the schematic on the right side of FIG. 2, the ligation strand of the P2 adaptor is ligated to the unmarked antisense strand (first strand product).

In the methods illustrated in both FIGS. 1 and 2, the duplex adaptors are unphosphorylated and thus do not contain free 5' phosphate groups. As such, both adaptors (P1/P2) contain a strand (the ligation strand) that will ligate with the free 5' phosphate on the double-stranded cDNA and a strand that does not ligate (non-ligation strand) to the double-stranded cDNA and thus leaves a gap. As such, in either orientation, the double-stranded cDNA containing the ligated adaptors is subjected to gap or fill-in repair (preferably with a DNA dependent DNA polymerase such as Taq DNA polymerase) in order to fill-in the gap through DNA dependent DNA polymerase mediated synthesis of the sequence of the non-ligation strand of the duplex adaptors using the respective ligation strand as template.

In both FIGS. 1 and 2, gap repair is followed by base excision via treatment with a cleavage agent, which can be an enzyme. In one embodiment as shown in FIGS. 1 and 2, base excision can be performed with an enzyme such as UNG. In a preferred embodiment, base excision can be followed by cleavage of the phosphodiester or DNA backbone using an enzyme, chemical agent, and/or heat at the site where the base was cleaved. In FIG. 1, base excision leads to the cleavage of the marked sense strand product, while both adaptors remain intact. In FIG. 2, base excision leads to the cleavage of both the marked sense strand product and the one adaptor that has dUTP incorporated into the ligation strand of said adaptor, while the adaptor that does not have dUTP incorporated into the ligation strand remains intact. In both FIGS. 1 and 2, the marked sense strand product or second strand product can be cleaved and thus only the antisense strand product or first strand product remains following base excision.

In contrast to FIG. 1 wherein both adaptor orientations remain intact following base excision, the schematic on the left side of FIG. 2 shows that the marked sense strand product can be cleaved along with the marked ligation strand of the P2 adaptor that is ligated to the sense strand product. As such, only the antisense strand product and the ligation strand of the adaptor ligated to the antisense strand (P1 in FIG. 2) remain intact and available for downstream processing. In a preferred embodiment downstream processing entails amplification of the remaining cDNA strand or antisense strand product. In contrast to FIG. 1 wherein amplification of the antisense strand product can be performed using primers complementary to sequence contained in either the ligation strand of the P1 adaptor (P1 amp) or P2 adaptor (P2 amp), FIG. 2 shows that amplification of the antisense strand product can only be performed using primers complementary to sequence contained in the ligation strand of the P1 adaptor (P1 amp). In a preferred embodiment, downstream processing can also entail sequencing of the antisense strand product (first strand product) and/or the amplified products. In FIG. 1, downstream sequencing using primers complementary to sequence in the ligation strand of the P1 adaptor will sequence either the sense or antisense strands relative to the RNA template. In FIG. 2, downstream sequencing using primers complementary to sequence in the ligation strand of the P1 adaptor will sequence only the antisense strand relative to the RNA template.

FIG. 4 illustrates a flow chart depicting one embodiment of the method for generating a directional strand specific cDNA library. The method involves the steps of generating first strand cDNA by performing random-primed reverse transcription on polyA+RNA; generating $2^{nd}$ strand cDNA using a DNA-dependent DNA polymerase using dATP, dCTP, dGTP, and dUTP in place of dTTP; fragmenting the double-stranded cDNA using sonication; end-repairing the purified fragmented double-stranded cDNA to generate blunt ends; ligating duplex adaptors wherein one of the ligation strands of one of the duplex adaptors is marked via incorporation of dUTP; nick repairing the ligation products to generate double-stranded cDNA containing the ligated adaptors; performing strand selection of the purified double-stranded cDNA containing the ligated adaptors using an enzyme and/or chemical agent; amplifying the remaining cDNA strand using PCR.

In an aspect to any of the embodiments above, the directional cDNA libraries created by the methods described herein can be depleted of non-desired nucleic acid sequences. In one embodiment, the non-desired nucleic acid comprises RNA. In a preferred embodiment, the non-desired nucleic acid comprises ribosomal or rRNA. Removal or depletion of rRNA from the directional cDNA libraries generated by the methods of the present invention can be performed by any of the methods known in the art including, but not limited to, removal of rRNA from the starting population, differential priming using oligo dT primers (i.e. priming polyadenylated transcripts only), and/or differential priming where primers complementary to rRNA sequences are specifically eliminated (or under-represented) in a primer pool (Not-So-Random or NSR primer approach).

In general, the methods described herein can be used to create nucleic acid libraries preferentially populated with nucleic acids of specific strand orientations relative to the nucleic acid template from which the library was generated. The nucleic acid libraries generated by the methods described herein can be used to ascertain the directionality and strand orientation of the nucleic acid template. In one embodiment, the nucleic acid template can be an RNA template and the nucleic acid library can be a cDNA library. In a preferred embodiment, the RNA template can be non-rRNA. In yet another preferred embodiment, the RNA template can be rRNA. In an aspect of the methods described herein, the cDNA library can be a directional cDNA library that retains the directionality and strand information pertaining to the original RNA template or sample, that is to say, the directional library of the methods of the invention represents products generated from first strand cDNA, or reverse transcription of the template RNA, or the second strand cDNA (a copy of the first strand cDNA). The methods of the invention provide means for exclusive retention of either first strand cDNA products or second strand cDNA products, thus enabling assigning the directionality of transcription from the genomic DNA. The directionality of transcription is inferred from the knowledge of which of the cDNA strand (first or second strand) is represented in the sequence information. The directionality and strand information of the RNA template can refer to the strand of genomic DNA from which the RNA template was derived or transcribed. As a further aspect of the methods described herein, the directional cDNA library can be used to determine the directionality of transcription by comparing the sequence of cDNAs in the directional cDNA library to the RNA template and/or genomic DNA. Methods of comparing nucleotide sequences are known in the art and can include well known nucleotide sequence alignment programs or algorithms such as the BLAST algorithm from NCB1.

Based on the methods described herein, the retention of the directionality and strand information of the RNA template can be determined with greater than 50% efficiency. The efficiency of retention of directionality and strand orientation using the methods described herein can be >50%, >55%, >60%, >65%, >70%, >75%, >80%, >85%, >90%, or >95%. The efficiency of retention of directionality and strand orientation can be >99%. The methods described herein can be used to generate directional cDNA libraries wherein greater than 50% of the cDNAs in the cDNA library comprise a specific strand orientation. The retention of a specific strand orientation using the methods described herein can be >50%, >55%, >60%, >65%, >70%, >75%, >80%, >85%, >90%, or >95%. The retention of specific strand orientation of cDNAs in the directional cDNA library can be >99%. As illustrated in FIG. 3, the methods of the present invention were used to generate directional cDNA libraries designed to retain the antisense strand product or first strand cDNA. As shown in FIG. 3, >97% of the sequence reads that mapped to the coding exons of human mRNAs from which the cDNAs were derived where in the antisense orientation.

Unless otherwise specified, terms and symbols of genetics, molecular biology, biochemistry and nucleic acid used herein follow those of standard treatises and texts in the field, e.g. Kornberg and Baker, *DNA Replication*, Second Edition (W.H. Freeman, New York, 1992); Lehninger, *Biochemistry*, Second Edition (Worth Publishers, New York, 1975); Strachan and Read, Human *Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

RNA Sample

The RNA sample of the present invention can be double-stranded, partially double-stranded; and single-stranded nucleic acids from any source including, but not limited to, synthetic or semisynthetic nucleic acids in purified or unpurified form, which can be DNA (dsDNA and ssDNA) or RNA, including tRNA, mRNA, rRNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof. Exemplary starting material comprising DNA (including genomic DNA) can be transcribed into RNA form, which can be achieved using methods disclosed in Kurn, U.S. Pat. No. 6,251,639, and by other techniques, such as expression systems. RNA copies of genomic DNA would generally include untranscribed sequences generally not found in mRNA, such as introns, regulatory and control elements, etc. Exemplary RNA samples can be obtained and purified using standard techniques in the art and includes RNAs in purified or unpurified form, which include, but are not limited to, mRNAs, tRNAs, snRNAs, rRNAs, retroviruses, small non-coding RNAs, microRNAs, polysomal RNAs, pre-mRNAs, intronic RNA, viral RNA, cell free RNA and fragments thereof. In one embodiment, the RNA sample provided for the methods of the present invention includes a whole transcriptome which can include tRNA, mRNA, rRNA, and non-coding RNA. The non-coding RNA, or ncRNA may include snoRNAs, microRNAs, siRNAs, piRNAs and long nc RNAs. In a preferred embodiment, the RNA sample has the rRNA content reduced or removed using standard techniques in the art. In a most preferred embodiment, the RNA sample is mRNA.

Primers

The term "primer", as used herein, can refer to a nucleotide sequence, generally with a free 3' hydroxyl group, that is capable of hybridizing with a template (such as one or more target polynucleotides, one or more target DNAs, one or more target RNAs or a primer extension product) and is also capable of promoting polymerization of a polynucleotide complementary to the template. A primer can be, for example, an oligonucleotide. It can also be, for example, a sequence of the template (such as a primer extension product or a fragment of the template created following RNase [i.e. RNase H] cleavage of a template-DNA complex) that is hybridized to a sequence in the template itself (for example, as a hairpin loop), and that is capable of promoting nucleotide polymerization. Thus, a primer can be an exogenous (e.g., added) primer or an endogenous (e.g., template fragment) primer. A primer may contain a non-hybridizing sequence that constitutes a tail of the primer. A primer may still be hybridizing to a target even though its sequences are not fully complementary to the target.

The primers of the invention are generally oligonucleotides that are employed in an extension reaction by a polymerase along a polynucleotide template, such as in PCR, SPIA or cDNA synthesis, for example. The oligonucleotide primer can be a synthetic polynucleotide that is single stranded, containing a sequence at its 3'-end that is capable of hybridizing with a sequence of the target polynucleotide. Normally, the 3' region of the primer that hybridizes with the target nucleic acid has at least 80%, preferably 90%, more preferably 95%, most preferably 100%, complementarity to a sequence or primer binding site.

"Complementary", as used herein, can refer to complementarity to all or only to a portion of a sequence. The number of nucleotides in the hybridizable sequence of a specific oligonucleotide primer should be such that stringency conditions used to hybridize the oligonucleotide primer will prevent excessive random non-specific hybridization. Usually, the number of nucleotides in the hybridizing portion of the oligonucleotide primer will be at least as great as the defined sequence on the target polynucleotide that the oligonucleotide primer hybridizes to, namely, at least 5, at least 6, at least 7, at least 8, at least 9, at least 10, at least 11, at least 12, at least 13, at least 14, at least 15, at least about 20, and generally from about 6 to about 10 or 6 to about 12 or 12 to about 200 nucleotides, usually about 20 to about 50 nucleotides. In general, the target polynucleotide is larger than the oligonucleotide primer or primers as described previously.

In some cases, the identity of the investigated target polynucleotide sequence is known, and hybridizable primers can be synthesized precisely according to the antisense sequence of the aforesaid target polynucleotide sequence. In other cases, when the target polynucleotide sequence is unknown, the hybridizable sequence of an oligonucleotide primer is a random sequence. Oligonucleotide primers comprising random sequences may be referred to as "random primers", as described herein. In yet other cases, an oligonucleotide primer such as a first primer or a second primer comprises a set of primers such as for example a set of first primers or a set of second primers. In some cases, the set of first or second primers may comprise a mixture of primers designed to hybridize to a plurality (e.g. 2, 3, 4, about 6, 8, 10, 20, 40, 80, 100, 125, 150, 200, 250, 300, 400, 500, 600, 800, 1000, 1500, 2000, 2500, 3000, 4000, 5000, 6000, 7000, 8000, 10,000, 20,000, 25,000 or more) of target sequences. In some cases, the plurality of target sequences may comprise a group of related sequences, random sequences, a whole transcriptome or fraction (e.g. substantial fraction) thereof, or any group, of sequences such as mRNA.

Tailed primers can be employed in certain embodiments of the invention. In general, a tailed primer comprises a 3' portion that is hybridizable to one or more target polynucleotides, such as one or more target RNAs in an RNA sample, and a 5' portion that is not hybridizable to the one or more target polynucleotides. In general, the non-hybridizable 5' portion does not hybridize to the one or more target polynucleotides under conditions in which the hybridizable 3' portion of the tailed primer hybridizes to the one or more target polynucleotides. In some embodiments, the non-hybridizable 5' portion comprises a promoter-specific sequence. Generally, a promoter-specific sequence comprises a single-stranded DNA sequence region which, in double-stranded form is capable of mediating RNA transcription. Examples of promoter-specific sequences are known in the art, and include, without limitation, T7, T3, or SP6 RNA polymerase promoter sequences. When the tailed primer is extended with a DNA polymerase, a primer extension product with a 5' portion comprising a defined sequence can be created. This primer extension product can then have a second primer anneal to it, which can be extended with a DNA polymerase to create a double stranded product comprising a defined sequence at one end. In some embodiments, where the non-hybridizable 5' portion of one or more tailed primers comprises a promoter-specific sequence, creation of a double-stranded product comprising a defined sequence at one end generates a double-stranded promoter sequence that is capable of mediating RNA transcription. In some embodiments, a double-stranded promoter sequence can be generated by hybridizing to the promoter-specific sequence an oligonucleotide comprising a sequence complementary to the promoter-specific sequence. In some embodiments, formation of a double-stranded promoter can be followed by the generation of single-stranded RNA by RNA transcription of sequence downstream of the double-stranded promoter, generally in a reaction mixture comprising all necessary components, including but not limited to ribonucleoside triphosphates (rNTPs) and a DNA-dependent RNA polymerase. Tailed primers can comprise DNA, RNA, or both DNA and RNA. In some embodiments, the tailed primer consists of DNA.

Composite primers can be employed in certain embodiments of the invention. Composite primers are primers that are composed of RNA and DNA portions. In some aspects, the composite primer can be a tailed composite primer comprising, for example, a 3'-DNA portion and a 5'-RNA portion. In the tailed composite primer, a 3'-portion, all or a portion of which comprises DNA, is complementary to a polynucleotide; and a 5'-portion, all or a portion of which comprises RNA, is not complementary to the polynucleotide and does not hybridize to the polynucleotide under conditions in which the 3'-portion of the tailed composite primer hybridizes to the polynucleotide target. When the tailed composite primer is extended with a DNA polymerase, a primer extension product with a 5'-RNA portion comprising a defined sequence can be created. This primer extension product can then have a second primer anneal to it, which can be extended with a DNA polymerase to create a double stranded product with an RNA/DNA heteroduplex comprising a defined sequence at one end. The RNA portion can be selectively cleaved from the partial heteroduplex to create a double-stranded DNA with a 3'-single-stranded overhang which can be useful for various aspects of the present invention including allowing for isothermal amplification using a composite amplification primer.

In other aspects, the composite primer can be an amplification composite primer (interchangeably called composite amplification primer). In the amplification composite primer, both the RNA and the DNA portions are generally complementary and hybridize to a sequence in the polynucleotide to be copied or amplified. In some embodiments, a 3'-portion of the amplification composite primer is DNA and a 5'-portion of the composite amplification primer is RNA. The composite amplification primer is designed such that the primer is extended from the 3'-DNA portion to create a primer extension product. The 5'-RNA portion of this primer extension product, in a RNA/DNA heteroduplex is susceptible to cleavage by RNase H, thus freeing a portion of the polynucleotide to the hybridization of an additional composite amplification primer. The extension of the amplification composite primer by a DNA polymerase with strand displacement activity releases the primer extension product from the original primer and creates another copy of the sequence of the polynucleotide. Repeated rounds of primer hybridization, primer extension with strand displacement DNA synthesis, and RNA cleavage create multiple copies of the sequence of the polynucleotide. Composite primers are described in more detail below.

A "random primer," as used herein, can be a primer that generally comprises a sequence that is designed not necessarily based on a particular or specific sequence in a sample, but rather is based on a statistical expectation (or an empirical observation) that the sequence of the random primer is hybridizable (under a given set of conditions) to one or more sequences in the sample. A random primer will generally be an oligonucleotide or a population of oligonucleotides comprising a random sequence(s) in which the nucleotides at a given position on the oligonucleotide can be any of the four nucleotides, or any of a selected group of the four nucleotides (for example only three of the four nucleotides, or only two of the four nucleotides). In some cases all of the positions of the oligonucleotide or population of oligonucleotides can be any of two or more nucleotides. In other cases, only a portion of the oligonucleotide, for instance a particular region, will comprise positions which can be any of two or more bases. In some cases, the portion of the oligonucleotide which comprises positions which can be any of two or more bases is about 5, 6, 7, 8, 9, 10, 11, 12, 13, 14, or about 15-20 nucleotides in length. In some cases, a random primer may comprise a tailed primer having a 3'-region that comprises a random sequence and a 5'-region that is a non-hybridizing sequence that comprises a specific, non-random sequence. The 3'-region may also comprise a random sequence in combination with a region that comprises poly-T sequences. The sequence of a random primer (or its complement) may or may not be naturally-occurring, or may or may not be present in a pool of sequences in a sample of interest. The amplification of a plurality of RNA species in a single reaction mixture can employ, but not necessarily employ, a multiplicity, preferably a large multiplicity, of random primers. As is well understood in the art, a "random primer" can also refer to a primer that is a member of a population of primers (a plurality of random primers) which collectively are designed to hybridize to a desired and/or a significant number of target sequences. A random primer may hybridize at a plurality of sites on a nucleic acid sequence. The use of random primers provides a method for generating primer extension products complementary to a target polynucleotide which does not require prior knowledge of the exact sequence of the target. In some embodiments one portion of a primer is random, and another portion of the primer comprises a defined sequence. For example, in some embodiments, a 3'-portion of the primer will comprise a random sequence, while the 5'-portion of the primer comprises a defined sequence. In some embodiments a 3'-random portion of the primer will comprise DNA, and a 5'-defined portion of the primer will comprise RNA, in other embodiments, both the 3' and 5'-portions will comprise DNA. In some embodiments, the 5'-portion will contain a defined sequence and the 3'-portion will comprise a poly-dT sequence that is hybridizable to a multiplicity of RNAs in a sample (such as all mRNA). In some embodiments, a "random primer," or primer comprising a randomly generated sequence, comprises a collection of primers comprising one or more nucleotides selected at random from two or more different nucleotides, such that all possible sequence combinations of the nucleotides selected at random may be represented in the collection. In some embodiments, generation of one or more random primers does not include a step of excluding or selecting certain sequences or nucleotide combinations from the possible sequence combinations in the random portion of the one or more random primers.

In one embodiment, the primers of the invention can be tailed primers. In this embodiment, the 5'-tail can comprise RNA and is non hybridizable to the RNA in the sample. The 3'-end of the first primer(s) can be hybridizable to the RNA in the sample, comprise DNA and comprise a random sequence, enabling hybridization across the whole transcriptome. The first primer may also comprise a mixture of primers. The mixture of first primers may also include a first primer comprising a 3'-DNA sequence hybridizable to the 3'-poly A tail of mRNA, in addition to the first primers comprising a random sequence at the 3'-ends.

In certain embodiments of the invention, the polynucleotide template for the polymerase reaction can be a RNA molecule with a poly(A) tail. In such cases, it is preferred that the primers are oligo(dT), oligo(dU) or oligo(U) primers, or, alternatively, composite primers with oligo d(T), oligo(dU) or oligo(U) region on the 3' end of the primer.

In another embodiment of the invention, the polynucleotide template for the polymerase reaction can be a RNA molecule without a poly(A) tail. In such cases, it is preferred that the primers are random primers, or, alternatively, composite primers with a random sequence that is hybridizable to the RNA in the sample on the 3' end of the primer.

In certain other embodiments of the invention, the polynucleotide template for the polymerase reaction can be a cDNA molecule. In such cakes, it is preferred that the primers are random primers, or, alternatively, composite primers such as the amplication composite primers described herein with a random sequence that is hybridizable to a portion of the cDNA template on the 3' end of the primer. In yet another embodiment, the polynucleotide template for the polymerase reaction is a cDNA molecule whose sequence is known. In such cases, it is preferred that the primers contain sequences complementary to all or a portion of the known sequence of the target polynucleotide or, alternatively, composite primers such as the amplication composite primers described herein with a sequence that is complementary to a portion of the cDNA template whose sequence is known on the 3' end of the primer.

RNA-Dependent DNA Polymerases

RNA-dependent DNA polymerases for use in the methods and compositions of the invention are capable of effecting extension of a primer according to the methods of the invention. Accordingly, a preferred RNA-dependent DNA polymerasecan be one that is capable of extending a nucleic acid primer along a nucleic acid template that is comprised at least predominantly of ribonucleotides. Suitable RNA-dependent DNA polymerases for use in the methods and compositions of the invention include reverse transcriptases (RTs). RTs are well known in the art. Examples of RTs include, but are not limited to, Moloney murine leukemia virus (M-MLV) reverse transcriptase, human immunodeficiency virus (HIV) reverse transcriptase, rous sarcoma virus (RSV) reverse transcriptase, avian myeloblastosis virus (AMV) reverse transcriptase, rous associated virus (RAV) reverse transcriptase, and myeloblastosis associated virus (MAV) reverse transcriptase or other avian sarcoma-leukosis virus (ASLV) reverse transcriptases, and modified RTs derived therefrom. See e.g. U.S. Pat. No. 7,056,716. Many reverse transcriptases, such as those from avian myeoloblastosis virus (AMV-RT), and Moloney murine leukemia virus (MMLV-RT) comprise more than one activity (for example, polymerase activity and ribonuclease activity) and can function in the formation of the double stranded cDNA molecules. However, in some instances, it is preferable to employ a RT which lacks or has substantially reduced RNase H activity. RTs devoid of RNase H activity are known in the art, including those comprising a mutation of the wild type reverse transcriptase where the mutation eliminates the RNase H activity. Examples of RTs having reduced RNase H activity are described in US20100203597. In these cases, the addition of an RNase H from other sources, such as that isolated from E. coli, can be employed for the degradation of the starting RNA sample and the formation of the double stranded cDNA. Combinations of RTs are also contemplated, including combinations of different non-mutant RTs, combinations of different mutant RTs, and combinations of one or more non-mutant RT with one or more mutant RT.

DNA-Dependent DNA Polymerases

DNA-dependent DNA polymerases for use in the methods and compositions of the invention are capable of effecting extension of a primer according to the methods of the invention. Accordingly, a preferred DNA-dependent DNA polymerase can be one that is capable of extending a nucleic acid primer along a first strand cDNA in the presence of the RNA template or after selective removal of the RNA template. Exemplary DNA dependent DNA polymerases suitable for the methods of the present invention include but are not limited to Klenow polymerase, with or without 3'-exonuclease, Bst DNA polymerase, Bca polymerase, .phi.29 DNA polymerase, Vent polymerase, Deep Vent polymerase, Taq polymerase, T4 polymerase, and E. coli DNA polymerase 1, derivatives thereof, or mixture of polymerases. In some cases, the polymerase does not comprise a 5'-exonuclease activity. In other cases, the polymerase comprises 5' exonuclease activity. In some cases, the primer extension of the present invention may be performed using a polymerase comprising strong strand displacement activity such as for example Bst polymerase. In other cases, the primer extension of the present invention may be performed using a polymerase comprising weak or no strand displacement activity. One skilled in the art may recognize the advantages and disadvantages of the use of strand displacement activity during the primer extension step, and which polymerases may be expected to provide strand displacement activity (see e.g., New England Biolabs Polymerases). For example, strand displacement activity may be useful in ensuring whole transcriptome coverage during the random priming and extension step. Strand displacement activity may further be useful in the generation of double stranded amplification products during the priming and extension step. Alternatively, a polymerase which comprises weak or no strand displacement activity may be useful in the generation of single stranded nucleic acid products during primer hybridization and extension that are hybridized to the template nucleic acid.

In one embodiment, the double stranded products generated by the methods of the present invention can be end repaired to produce blunt ends for the adaptor ligation applications of the present invention. Generation of the blunt ends on the double stranded products may be generated by the use of a single strand specific DNA exonuclease such as for example exonuclease 1, exonuclease 7 or a combination thereof to degrade overhanging single stranded ends of the double stranded products. Alternatively, the double stranded products may be blunt ended by the use of a single stranded specific DNA endonuclease for example but not limited to mung bean endonuclease or S1 endonuclease. Alternatively, the double stranded products may be blunt ended by the use of a polymerase that comprises single stranded exonuclease activity such as for example T4 DNA polymerase, any other polymerase comprising single stranded exonuclease activity or a combination thereof to degrade the overhanging single stranded ends of the double stranded products. In some cases, the polymerase comprising single stranded exonuclease activity may be incubated in a reaction mixture that does or does not comprise one or more dNTPs. In other cases, a combination of single stranded nucleic acid specific exonucleases and one or more polymerases may be used to blunt end the double stranded products of the primer extension reaction. In still other cases, the products of the extension reaction may be made blunt ended by filling in the overhanging single stranded ends of the double stranded products. For example, the fragments may be incubated with a polymerase such as T4 DNA polymerase or Klenow polymerase or a combination thereof in the presence of one or more dNTPs to fill in the single stranded portions of the double stranded products. Alternatively, the double stranded products may be made blunt by a combination of a single stranded overhang degradation reaction using exonucleases and/or polymerases, and a fill-in reaction using one or more polymerases in the presence of one or more dNTPs.

In another embodiment, the adaptor ligation applications of the present invention can leave a gap between a non-ligation strand of the adaptors and a strand of the double stranded product of the present invention. In these instances, a gap repair or fill-in reaction may be necessary to append the double stranded product with the sequence of the non-ligation strand of the adaptor. Gap repair can be performed with any number of DNA dependent DNA polymerase described herein. In one embodiment, gap repair can be performed with a DNA dependent DNA polymerase with strand displacement activity. In one embodiment, gap repair can be performed using a DNA dependent DNA polymerase with weak or no strand displacement activity. In one embodiment, the ligation strand of the adaptor can serve as the template for the gap repair or fill-in reaction. In a preferred embodiment, gap repair can be performed using Taq DNA polymerase.

Methods of Strand-specific Selection

The compositions and methods provided herein are useful for retaining directional information in double-stranded DNA.

The term "strand specific" or "directional", as used herein, can refer to the ability to differentiate in a double-stranded polynucleotide between the original template strand and the strand that is complementary to the original template strand.

In some embodiments, the methods of the invention can be used to preserve information about the direction of single-stranded nucleic acid molecules while generating double-stranded polynucleotides more suitable for molecular cloning applications. One of the strands of the double-stranded polynucleotide can be synthesized so that it has at least one modified nucleotide incorporated into it along the entire length of the strand. In some embodiments, the incorporation of the modified nucleotide marks the strand for degradation or removal.

The term "first strand synthesis" can refer to the synthesis of the first strand using the original nucleic acid (RNA or DNA) as a starting template for the polymerase reaction. The nucleotide sequence of the first strand corresponds to the sequence of the complementary strand.

The term "second strand synthesis" can refer to the synthesis of the second strand that uses the first strand as a template for the polymerase reaction. The nucleotide sequence of the second strand corresponds to the sequence of the original nucleic acid template.

The term "unmodified dNTPs" or "classic dNTPs" can refer to the four deoxyribonucleotide triphosphates dATP (deoxyadenosine triphosphate), dCTP (deoxycytidine triphosphate), dGTP (deoxyguanosine triphosphate) and dTTP (deoxythymidine triphosphate) that are normally used as building blocks in the synthesis of DNA. Similarly, the term "canonical dNTP" or "canonical nucleotide" can be used to refer to the four deoxyribonucleotide triphosphates dATP, dCTP, dGTP and dTTP that are normally found in DNA.

The term "canonical", as used herein, can refer to the nucleic acid bases adenine, cytosine, guanine and thymine that are commonly found in DNA or their deoxyribonucleotide or deoxyribonucleoside analogs. The term "non-canonical" can refer to nucleic acid bases in DNA other than the four canonical bases in DNA, or their deoxyribonucleotide or deoxyribonucleoside analogs. Although uracil is a common nucleic acid base in RNA, uracil is a non-canonical base in DNA.

The term "modified nucleotide" or "modified dNTP", as used herein, can refer to any molecule suitable for substituting one corresponding unmodified or classic dNTP. Such modified nucleotides must be able to undergo a base pair matching identical or similar to the classic or unmodified dNTP it replaces. The modified nucleotide or dNTP must be suitable for specific degradation or cleavage in which it is selectively degraded or cleaved by a suitable degrading or cleavageagent, thus rendering the DNA strand containing at least one modified and degraded or cleaved dNTP essentially unfit for amplification, sequencing, and/or hybridization. Alternatively, the modified nucleotide must mark the DNA strand containing the modified nucleotide eligible for selective removal or cleavage or facilitate separation of the polynucleotide strands. Such a removal or cleavage or separation can be achieved by molecules, particles or enzymes interacting selectively with the modified nucleotide, thus selectively removing or marking for removal or cleaving only one polynucleotide strand.

As used in this application, the term "strand marking" can refer to any method for distinguishing between the two strands of a double-stranded polynucleotide. The term "selection" can refer to any method for selecting between the two strands of a double-stranded polynucleotide. The term "selective removal" or "selective marking for removal" or "cleavage" can refer to any modification to a polynucleotide strand that renders that polynucleotide strand unsuitable for a downstream application, such as amplification or hybridization or sequencing.

The selective removal or cleavage of a marked strand in the present invention can be achieved through the use of enzymatic treatment of the marked strand. Enzymes that can be used for selective removal or cleavage of the marked strand according to the methods of the present invention can include glycosylases such as Uracil-N-Glycosylase (UNG), which selectively degrades the base portion of dUTP from the DNA backbone. Additional glycosylases which can be used in the methods of the present invention and their non-canonical or modified nucleotide substrates include 5-methylcytosine DNA glycosylase (5-MCDG), which cleaves the base portion of 5-methylcytosine (5-MeC) from the DNA backbone (Wolffe et al., Proc. Nat. Acad. Sci. USA 96:5894-5896, 1999); 3-methyladenosine-DNA glycosylase I, which cleaves the base portion of 3-methyl adenosine from the DNA backbone (see, e.g. Hollis et al (2000) Mutation Res. 460: 201-210); and/or 3-methyladenosine DNA glycosylase II, which cleaves the base portion of 3-methyladenosine, 7-methylguanine, 7-methyladenosine, and/3-methylguanine from the DNA backbone. See McCarthy et al (1984) EMBO J. 3:545-550. Multifunctional and mono-functional forms of 5-MCDG have been described. See Zhu et al., Proc. Natl. Acad. Sci. USA 98:5031-6, 2001; Zhu et al., Nuc. Acid Res. 28:4157-4165, 2000; and Neddermann et al., J. B. C. 271: 12767-74, 1996 (describing bifunctional 5-MCDG; Vairapandi & Duker, Oncogene 13:933-938, 1996; Vairapandi et al., J. Cell. Biochem. 79:249-260, 2000 (describing monofunctional enzyme comprising 5-MCDG activity). In some embodiments, 5-MCDG preferentially cleaves fully methylated polynucleotide sites (e.g., CpG dinucleotides), and in other embodiments, 5-MCDG preferentially cleaves a hemimethylated polynucleotide. For example, mono-functional human 5-methylcytosine DNA glycosylase cleaves DNA specifically at fully methylated CpG sites, and is relatively inactive on hemimethylated DNA (Vairapandi & Duker, supra; Vairapandi et al., supra). By contrast, chick embryo 5-methylcytosine-DNA glycosylase has greater activity directed to hemimethylated methylation sites. In some embodiments, the activity of 5-MCDG is potentiated (increased or enhanced) with accessory factors, such as recombinant CpG-rich RNA, ATP, RNA helicase enzyme, and proliferating cell nuclear antigen (PCNA). See U.S. Patent Publication No. 20020197639 A1. One or more agents may be used. In some embodiments, the one or more agents cleave a base portion of the same methylated nucleotide. In other embodiments, the one or more agents cleave a base portion of different methylated nucleotides. Treatment with two or more agents may be sequential or simultaneous.

In some embodiments of the present invention the generation of an abasic site in the DNA backbone through the removal or cleavage of the base portion of at least one modified nucleotide (i.e. dUTP) can be followed by fragmentation or cleavage of the backbone at the abasic site. Suitable agents (for example, an enzyme, a chemical and/or reaction conditions such as heat) capable of cleavage of the backbone at an abasic site include: heat treatment and/or chemical treatment (including basic conditions, acidic conditions, alkylating conditions, or amine mediated cleavage of abasic sites, (see e.g., McHugh and Knowland, Nucl. Acids Res. (1995) 23(10):1664-1670; Bioorgan. Med. Chem. (1991) 7:2351; Sugiyama, Chem. Res. Toxicol. (1994) 7: 673-83; Horn, Nucl. Acids. Res., (1988) 16:11559-71), and/or the use of enzymes that catalyze cleavage of polynucleotides at abasic sites, For example AP endonucleases (also called "apurinic, apyrimidinic endonucleases") (e.g., *E. coli* Endonuclease IV, available from Epicentre Tech., Inc, Madison Wis.), *E. coli* endonuclease 111 or endonuclease IV, *E. coli* exonuclease III in the presence of calcium ions. See, e.g. Lindahl, PNAS (1974) 71(9):3649-3653; Jendrisak, U.S. Pat. No. 6,190,865 BI; Shida, Nucleic Acids Res. (1996) 24(22):4572-76; Srivastava, J. Biol. Chem. (1998) 273(13):21203-209; Carey, Biochem. (1999) 38:16553-60; Chem Res Toxicol (1994) 7:673-683. As used herein "agent" encompasses reaction conditions such as heat. In one embodiment, the AP endonuclease, *E. coli* endonuclease IV, is used to cleave the phosphodiester backbone or phosphodiester bond at an abasic site. In another embodiment, cleavage is with an amine, such as N,N'-dimethylethylenediamine (DMED). See, e.g., McHugh and Knowland, supra.

In some cases, the nucleic acid comprising one or more abasic sites may be treated with a nucleophile or a base. In some cases, the nucleophile is an amine such as a primary amine, a secondary amine, or a tertiary amine. For example, the abasic site may be treated with piperidine, morpholine, or a combination thereof. In some cases, hot piperidine (e.g., 1M at 90° C.) may be used to cleave the nucleic acid comprising one or more abasic sites. In some cases, morpholine (e.g., 3M at 37° C. or 65° C.) may be used to cleave the nucleic acid comprising one or more abasic sites. Alternatively, a polyamine may be used to cleave the nucleic acid comprising one or more abasic sites. Suitable polyamines include for example spermine, spermidine, 1,4-diaminobutane, lysine, the tripeptide K—W—K, DMED, piperazine, 1,2-ethylenediamine, or any combination thereof. In some cases, the nucleic acid comprising one or more abasic sites may be treated with a reagent suitable for carrying out a beta elimination reaction, a delta elimination reaction, or a combination thereof. In some cases, the methods of the present invention provide for the use of an enzyme or combination of enzymes and a polyamine such as DMED under mild conditions in a single reaction mixture which does not affect the canonical or unmodified nucleotides and therefore may maintain the sequence integrity of the products of the method. Suitable mild conditions may include conditions at or near neutral pH. Other suitable conditions include pH of about 4.5 or higher, 5 or higher, 5.5 or higher, 6 or higher, 6.5 or higher, 7 or higher, 7.5 or higher, 8 or higher, 8.5 or higher, 9 or higher, 9.5 or higher, 10 or higher, or about 10.5 or higher. Still other suitable conditions include between about 4.5 and 10.5, between about 5 and 10.0, between about 5.5 and 9.5, between about 6 and 9, between about 6.5 and 8.5, between about 6.5 and 8.0, or between about 7 and 8.0. Suitable mild conditions also may include conditions at or near room temperature. Other suitable conditions include a temperature of about 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., or 70° C. or higher. Still other suitable conditions include between about 10° C. and about 70° C., between about 15° C. and about 65° C., between about 20° C. and about 60° C., between about 20° C. and about 55° C., between about 20° C. and about 50° C., between about 20° C. and about 45° C., between about 20° C. and about 40° C., between about 20° C. and about 35° C., or between about 20° C. and about 30° C. In some cases, the use of mild cleavage conditions may provide for less damage to the primer extension products produced by the methods of the present invention. In some cases, the fewer damaged bases, the more suitable the primer extension products may be for downstream analysis such as sequencing. In other cases, the use of mild cleavage conditions may increase final product yields, maintain sequence integrity, or render the methods of the present invention more suitable for automation.

In embodiments involving fragmentation, the backbone of the polynucleotide comprising the abasic site is cleaved at the abasic site, whereby two or more fragments of the polynucleotide are generated. At least one of the fragments comprises an abasic site, as described herein. Agents that cleave the phosphodiester backbone or phosphodiester bonds of a polynucleotide at an abasic site are provided herein. In some embodiments, the agent is an AP endonuclease such as E. coli AP endonuclease IV. In other embodiments, the agent is DMED. In other embodiments, the agent is heat, basic condition, acidic conditions, or an alkylating agent. In still other embodiments, the agent that cleaves the phosphodiester backbone at an abasic site is the same agent that cleaves the base portion of a nucleotide to form an abasic site. For example, glycosylases of the present invention may comprise both a glycosylase and a lyase activity, whereby the glycosylase activity cleaves the base portion of a nucleotide (e.g., a modified nucleotide) to form an abasic site and the lyase activity cleaves the phosphodiester backbone at the abasic site so formed. In some cases, the glycosylase comprises both a glycosylase activity and an AP endonuclease activity.

Appropriate reaction media and conditions for carrying out the cleavage of a base portion of a non-canonical or modified nucleotide according to the methods of the invention are those that permit cleavage of a base portion of a non-canonical or modified nucleotide. Such media and conditions are known to persons of skill in the art, and are described in various publications, such as Lindahl, PNAS (1974) 71(9):3649-3653; and Jendrisak, U.S. Pat. No. 6,190,865 BI; U.S. Pat. No. 5,035, 996; and U.S. Pat. No. 5,418,149. In one embodiment, UDG (Epicentre Technologies, Madison Wis.) is added to a nucleic acid synthesis reaction mixture, and incubated at 37° C. for 20 minutes. In one embodiment, the reaction conditions are the same for the synthesis of a polynucleotide comprising a non-canonical or modified nucleotide and the cleavage of a base portion of the non-canonical or modified nucleotide. In another embodiment, different reaction conditions are used for these reactions. In some embodiments, a chelating regent (e.g. EDTA) is added before or concurrently with UNG in order to prevent a polymerase from extending the ends of the cleavage products.

In a one embodiment, the selection is done by incorporation of at least one modified nucleotide into one strand of a synthesized polynucleotide, and the selective removal is by treatment with an enzyme that displays a specific activity towards the at least one modified nucleotide. In a preferred embodiment, the modified nucleotide being incorporated into one strand of the synthesized polynucleotide is deoxyuridine triphosphate (dUTP), replacing dTTP in the dNTP mix, and the selective removal of the marked strand from downstream applications is carried by out by UNG. UNG selectively degrades dUTP while it is neutral towards other dNTPs and their analogs. Treatment with UNG results in the cleavage of the N-glycosylic bond and the removal of the base portion of dU residues, forming abasic sites. In a preferred embodiment, the UNG treatment is done in the presence of an apurinic/apyrimidinic endonuclease (APE) to create nicks at the abasic sites. Consequently, a polynucleotide strand with incorporated dUTP that is treated with UNG/APE is cleaved and unable to undergo amplification by a polymerase. In another embodiment, nick generation and cleavage is achieved by treatment with a polyamine, such as DMED, or by heat treatment. In a preferred embodiment, UNG treatment is conducted in a reaction buffer containing 32 mM DMED.

As used in this application, the term "at least one nucleotide" or "at least one modified nucleotide" refers to a plurality of dNTP molecules of the same kind or species. Thus, use of "one modified nucleotide" refers to the replacement in the dNTP mix of one of the classic dNTPs dATP, dCTP, dGTP or dTTP with a corresponding modified nucleotide species. In a preferred embodiment, the at least one modified nucleotide is dUTP, replacing dTTP in the dNTP mix. In another embodiment, the at least one modified nucleotide is a biotinylated dNTP. In another embodiment, the at least one modified nucleotide contains a thio group. In another embodiment, the at least one modified nucleotide in an aminoallyl dNTP. In yet another embodiment, the at least one modified nucleotide is inosine, replacing dGTP in the dNTP mix. In some embodiments, the methods of the invention are used for construction of directional cDNA libraries. Strand marking is necessary, but not sufficient for construction of directional cDNA libraries when using adaptors that are not polarity-specific, i.e. adaptors generating ligation products with two adaptor orientations. Construction of directional cDNA libraries according to the methods of invention requires strand marking of both the cDNA insert and one of the two adaptors at the ligation strand of the adaptor. A useful feature of the present invention is the ability to switch around the adaptor orientation. For example, in a duplex adaptor system where P1/P2 designates adaptor orientation resulting in sense strand selection and (optional) sequencing, and where the P2 adaptor has at least one modified nucleotide incorporated along the ligation strand of the adaptor, modification of the protocol such that the P1 adaptor (as opposed to P2 adaptor) has at least one modified nucleotide incorporated along the ligation strand allows for antisense strand selection and (optional) sequencing.

In an embodiment where the second strand and one of the adaptors contains at least one modified nucleotide, the second strand and the one of the adaptors may be synthesized so that each comprises a sufficient and predictable density of modified nucleotides to provide for sufficient and predictable fragmentation, and when used with one or more agents capable of cleaving at the modified nucleotides (e.g., a glycosylase, a glycosylase and an amine, a glycosylase and heat, or a glycosylase and an AP endonuclease) to further generate fragments of desirable size range. Generally, a modified base can be incorporated at about every 5, 10, 15, 20, 25, 30, 40, 50, 65, 75, 85, 100, 123, 150, 175, 200, 225, 250, 300, 350, 400, 450, 500, 550, 600, 650 or more nucleotides apart in the resulting polynucleotide comprising a modified nucleotide. In one embodiment, the modified nucleotide is incorporated about every 200 nucleotides, about every 100 nucleotide, or about every 50, 25, 20, 15, 10, 9, 8, 7, 6, 5, or fewer nucleotides. In another embodiment, the modified nucleotide is incorporated about every 50 to about 200 nucleotides. In some embodiments, a 1:1, 1:2, 1:3, 1:4, 1:5, 1:6, 1:10, 1:15, 1:20 or higher ratio of modified to non-modified nucleotide may be used in the reaction mixture. In some cases, a 1:1, 1:2, 1:3, 1:4, 1:5, 1:6, 1:10, 1:15, 1:20 or higher ratio of the modified nucleotide dUTP to non-modified nucleotide dTTP is used in the reaction mixture.

The term "adaptor", as used herein, refers to an oligonucleotide of known sequence, the ligation of which to a target polynucleotide or a target polynucleotide strand of interest enables the generation of amplification-ready products of the target polynucleotide or the target polynucleotide strand of interest. Various adaptor designs are envisioned. Suitable adaptor molecules include single or double stranded nucleic acid (DNA or RNA) molecules or derivatives thereof, stem-loop nucleic acid molecules, double stranded molecules comprising one or more single stranded overhangs of 1, 2, 3, 4, 5, 6, 7, 8, 9, 10 bases or longer, proteins, peptides, aptamers, organic molecules, small organic molecules, or any adaptor molecules known in the art that may be covalently or non-covalently attached, such as for example by ligation, to the double stranded DNA fragments. The adaptors can be designed to comprise a double-stranded portion which can be ligated to double-stranded DNA (or double-stranded DNA with overhang) products. Various ligation processes and reagents are known in the art and can be useful for carrying out the methods of the invention. For example, blunt ligation can be employed. Similarly, a single dA nucleotide can be added to the 3'-end of the double-stranded DNA product, by a polymerase lacking 3'-exonuclease activity and can anneal to an adapter comprising a dT overhang (or the reverse). This design allows the hybridized components to be subsequently ligated (e.g., by T4 DNA ligase). Other ligation strategies and the corresponding reagents are known in the art and kits and reagents for carrying Out efficient ligation reactions are commercially available (e.g, from New England Biolabs, Roche). The double-stranded DNA portion of the adaptors can further comprise indexing or bar-coding sequences designed to mark either the samples or sequences of interest.

Blunt-end ligation with conventional duplex adaptors can be employed in the present invention, meaning that the adaptors are capable of ligation at either end of the target polynucleotide strand, thereby generating ligation products with two adaptor orientations. In a preferred embodiment, one of the two adaptors has at least one modified nucleotide incorporated along the ligation strand of the adaptor.

Methods of Amplification

The methods, compositions and kits described herein can be useful to generate amplification-ready products for downstream applications such as massively parallel sequencing (i.e. next generation sequencing methods) or hybridization platforms. Methods of amplification are well known in the art. Suitable amplification reactions can include any DNA amplification reaction, including but not limited to polymerase chain reaction (PCR), strand displacement amplification (SDA), linear amplification, multiple displacement amplification (MDA), rolling circle amplification (RCA), single primer isothermal amplification (SPIA, see e.g. U.S. Pat. No. 6,251,639), Ribo-SPIA, or a combination thereof: In some cases, the amplification methods for providing the template nucleic acid may be performed under limiting conditions such that only a few rounds of amplification (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 etc.), such as for example as is commonly done for cDNA generation. The number of rounds of amplification can be about 1-30, 1-20, 1-15, 1-10, 5-30, 10-30, 15-30, 20-30, 10-30, 15-30, 20-30, or 25-30.

PCR is an in vitro amplification procedure based on repeated cycles of denaturation, oligonucleotide primer annealing, and primer extension by thermophilic template dependent polynucleotide polymerase, resulting in the exponential increase in copies of the desired sequence of the polynucleotide analyte flanked by the primers. The two different PCR primers, which anneal to opposite strands of the DNA, are positioned so, that the polymerase catalyzed extension product of one primer can serve as a template strand for the other, leading to the accumulation of a discrete double stranded fragment whose length is defined by the distance between the 5' ends of the oligonucleotide primers.

LCR uses a ligase enzyme to join pairs of preformed nucleic acid probes. The probes hybridize with each complementary strand of the nucleic acid analyte, if present, and ligase is employed to bind each pair of probes together resulting in two templates that can serve in the next cycle to reiterate the particular nucleic acid sequence.

SDA (Westin et al 2000, Nature Biotechnology, 18, 199-202; Walker et al 1992, Nucleic Acids Research, 20, 7, 1691-1696), is an isothermal amplification technique based upon the ability of a restriction endonuclease such as HincII or BsoBI to nick the unmodified strand of a hemiphosphorothioate form of its recognition site, and the ability of an exonuclease deficient DNA polymerase such as Klenow exo minus polymerase, or Bst polymerase, to extend the 3'-end at the nick and displace the downstream DNA strand. Exponential amplification results from coupling sense and antisense reactions in which strands displaced from a sense reaction serve as targets for an antisense reaction and vice versa.

Some aspects of the invention utilize linear amplification of nucleic acids or polynucleotides. Linear amplification generally refers to a method that involves the formation of one or more copies of the complement of only one strand of a nucleic acid or polynucleotide molecule, usually a nucleic acid or polynucleotide analyte. Thus, the primary difference between linear amplification and exponential amplification is that in the latter process, the product serves as substrate for the formation of more product, whereas in the former process the starting sequence is the substrate for the formation of product but the product of the reaction, i.e. the replication of the starting template, is not a substrate for generation of products. In linear amplification the amount of product formed increases as a linear function of time as opposed to exponential amplification where the amount of product formed is an exponential function of time.

In some embodiments, the amplification is exponential, e.g. in the enzymatic amplification of specific double stranded sequences of DNA by a polymerase chain reaction (PCR). In other embodiments the amplification method is linear. In other embodiments the amplification method is isothermal.

Downstream Applications for Whole Transcriptome Analysis

An important aspect of the invention is that the methods and compositions disclosed herein can be efficiently and cost-effectively utilized for downstream analyses, such as next generation sequencing or hybridization platforms, with minimal loss of biological material of interest. Specifically, the methods of the invention are useful for sequencing a cDNA library or a whole transcriptome while retaining information on which strand was present in the original RNA sample. In one embodiment, the invention provides for a method for whole transcriptome sequencing comprising providing a RNA sample, providing one or more primers of known or unknown sequence, combining the one or more primers with a reverse transcriptase, reverse transcribing the sample, generating double-stranded cDNA from the reverse transcribed RNA sample, wherein at least one of the four dNTPs dATP, dCTP, dGTP or dTTP is replaced by a modified dNTP during second strand synthesis and incorporated into the second strand, performing end repair on the double-stranded cDNA, ligating adaptors to the double-stranded cDNA, wherein one of the adaptors has the modified dNTP incorporated into a ligation strand of the adaptor, performing gap repair, selectively removing or marking for removal the second strand by a suitable degrading agent, amplifying the RNA sample using one or more primers to produce amplified products, and performing sequencing on the products. In some embodiments, sequencing is performed on single-stranded cDNA as generated by the methods of the present invention without amplifying the RNA sample following selective removal of the marked second strand. In some embodiments, the starting amount of RNA is 0.01 ng to 100 mg. The primers used for reverse transcription and/or amplification can be tailed primers, chimeric primers, or tailed and chimeric primers.

In one embodiment, a collection of tailed primers, and a RT enzyme is provided, wherein the RT is used in combination with the tailed primers to reverse transcribe a whole transcriptome. In one embodiment, a collection of chimeric primers, each comprising RNA and DNA, and a RT enzyme is provided, wherein the RT is used in combination with the chimeric primers to reverse transcribe a whole transcriptome. In some embodiments, no more than 5%, 10%, 15%, 20%, 25%, 30%, 40%, 50%, 60%, 70%, 75%, 80% of the resulting products are rRNA sequences.

The methods of the invention can be useful for sequencing by the method commercialized by Illumina, as described in U.S. Pat. Nos. 5,750,341; 6,306,597; and 5,969,119. Directional (strand-specific) cDNA libraries are prepared using the methods of the present invention, and the selected single-stranded nucleic acid is amplified, for example, by PCR. The resulting nucleic acid is then denatured and the single-stranded amplified polynucleotides are randomly attached to the inside surface of flow-cell channels. Unlabeled nucleotides are added to initiate solid-phase bridge amplification to produce dense clusters of double-stranded DNA. To initiate the first base sequencing cycle, four labeled reversible terminators, primers, and DNA polymerase are added. After laser excitation, fluorescence from each cluster on the flow cell is imaged. The identity of the first base for each cluster is then recorded. Cycles of sequencing are performed to determine the fragment sequence one base at a time.

In some embodiments, the methods of the invention can be useful for preparing target polynucleotides for sequencing by the sequencing by ligation methods commercialized by Applied Biosystems (e.g., SOLiD sequencing). In other embodiments, the methods are useful for preparing target polynucleotides for sequencing by synthesis using the methods commercialized by 454/Roche Life Sciences, including but not limited to the methods and apparatus described in Margulies et al., *Nature* (2005) 437:376-380 (2005); and U.S. Pat. Nos. 7,244,559; 7,335,762; 7,211,390; 7,244,567; 7,264,929; and 7,323,305. In other embodiments, the methods can be useful for preparing target polynucleotide(s) for sequencing by the methods commercialized by Helicos BioSciences Corporation (Cambridge, Mass.) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058. In other embodiments, the methods can be useful for preparing target polynucleotide(s) for sequencing by the methods commercialized by Pacific Biosciences as described in U.S. Pat. Nos. 7,462,452; 7,476,504; 7,405,281; 7,170,050; 7,462,468; 7,476,503; 7,315,019; 7,302,146; 7,313,308; and US Application Publication Nos. US20090029385; US20090068655; US20090024331; and US20080206764.

Another example of a sequencing technique that can be used in the methods of the provided invention is nanopore sequencing (see e.g. Soni G V and Meller A. (2007) *Clin Chem* 53: 1996-2001). A nanopore can be a small hole of the order of 1 nanometer in diameter. Immersion of a nanopore in a conducting fluid and application of a potential across it can result in a slight electrical current due to conduction of ions through the nanopore. The amount of current that flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore can represent a reading of the DNA sequence.

Another example of a sequencing technique that can be used in the methods of the provided invention is semiconductor sequencing provided by Ion Torrent (e.g., using the Ion Personal Genome Machine (PGM)). Ion Torrent technology can use a semiconductor chip with multiple layers, e.g., a layer with micro-machined wells, an ion-sensitive layer, and an ion sensor layer. Nucleic acids can be introduced into the wells, e.g., a clonal population of single nucleic can be attached to a single bead, and the bead can be introduced into a well. To initiate sequencing of the nucleic acids on the beads, one type of deoxyribonucleotide (e.g., dATP, dCTP, dGTP, or dTTP) can be introduced into the wells. When one or more nucleotides are incorporated by DNA polymerase, protons (hydrogen ions) are released in the well, which can be detected by the ion sensor. The semiconductor chip can then be washed and the process can be repeated with a different deoxyribonucleotide. A plurality of nucleic acids can be sequenced in the wells of a semiconductor chip. The semiconductor chip can comprise chemical-sensitive field effect transistor (chemFET) arrays to sequence DNA (for example, as described in U.S. Patent Application Publication No. 20090026082). Incorporation of one or more triphosphates into a new nucleic acid strand at the 3' end of the sequencing primer can be detected by a change in current by a chemFET. An array can have multiple chemFET sensors.

Kits

Any of the compositions described herein may be comprised in a kit. In a non-limiting example, the kit, in a suitable container, comprises: one or more primers, a reverse transcription enzyme, and optionally reagents for amplification.

The containers of the kits can generally include at least one vial, test tube, flask, bottle, syringe or other containers, into which a component may be placed, and preferably, suitably aliquotted. Where there is more than one component in the kit, the kit also will generally contain a second, third or other additional container into which the additional components may be separately placed. However, various combinations of components may be comprised in a container.

When the components of the kit are provided in one or more liquid solutions, the liquid solution can be an aqueous solution. However, the components of the kit may be provided as dried powder(s). When reagents and/or components are provided as a dry powder, the powder can be reconstituted by the addition of a suitable solvent.

The present invention provides kits containing one or more compositions of the present invention and other suitable reagents suitable for carrying out the methods of the present invention. The invention provides, e.g., diagnostic kits for clinical or criminal laboratories, or nucleic acid amplification or analysis kits for general laboratory use. The present invention thus includes kits which include some or all of the reagents necessary to carry out the methods of the present invention, e.g., sample preparation reagents, oligonucleotides, binding molecules, stock solutions, nucleotides, polymerases, enzymes, positive and negative control oligonucleotides and target sequences, test tubes or plates, fragmentation reagents, detection reagents, purification matrices, and an instruction manual. In some embodiments, the kit of the present invention contains a non-canonical or modified nucleotide. Suitable non-canonical or modified nucleotides include any nucleotides provided herein including but not limited to dUTP, or a methylated purine.

In some embodiments, the kit may contain one or more reaction mixture components, or one or more mixtures of reaction mixture components. In some cases, the reaction mixture components or mixtures thereof may be provided as concentrated stocks, such as 1.1×, 1.5×, 2×, 2.5×, 3×, 4×, 5×, 6×, 7×, 10×, 15×, 20×, 25×, 33×, 50×, 75×, 100× or higher concentrated stock. The reaction mixture components may include any of the compositions provided herein including but not limited to buffers, salts, divalent cations, azeotropes, chaotropes, dNTPs, labeled nucleotides, non-canonical or modified nucleotides, dyes, fluorophores, biotin, enzymes (such as endonucleases, exonucleases, glycosylases), or any combination thereof.

In some embodiments, the kit may contain one or more oligonucleotide primers, such as the oligonucleotide primers provided herein. For example, the kit may contain one or more oligonucleotide primers comprising random hybridizing portions. Alternatively, the kit may contain oligonucleotide primers comprising polyT hybridizing portions. In some cases, the kit may contain oligonucleotide primers that comprise random hybridizing portions and primers comprising polyT hybridizing portions. In still other cases, the kit may contain "not so random" primers that have been preselected to hybridize to desired nucleic acids, but not hybridize to undesired nucleic acids. In some cases the kit may contain tailed primers comprising a 3'-portion hybridizable to the target nucleic acid and a 5'-portion which is not hybridizable to the target nucleic acid. In some cases, the kit may contain chimeric primers comprising an RNA portion and a DNA portion. In some cases, the kit may contain primers comprising non-canonical or modified nucleotides.

In some embodiments, the kit of the present invention may contain one or more polymerases or mixtures thereof. In some cases, the one or more polymerases or mixtures thereof may comprise strand displacement activity. Suitable polymerases include any of the polymerases provided herein. The kit may further contain one or more polymerase substrates such as for example dNTPs, non-canonical or modified nucleotides.

In some embodiments, the kit of the present invention may contain one or more means for purification of the nucleic acid products, removing of the fragmented products from the desired products, or combination of the above. Suitable means for the purification of the nucleic acid products include but are not limited to single stranded specific exonucleases, affinity matrices, nucleic acid purification columns, spin columns, ultrafiltration or dialysis reagents, or electrophoresis reagents including but not limited acrylamide or agarose, or any combination thereof.

In some embodiments, the kit of the present invention may contain one or more agents capable of cleaving the base portion of a non-canonical nucleotide to generate an abasic site. In some cases, this agent may comprise one or more glycosylases. Suitable glycosylases include any glycosylases provided herein including but not limited to UDG, or MPG.

In some embodiments, the kit of the present invention may contain one or more agents capable of fragmenting a phosphodiester backbone at an abasic site to fragment the input nucleic acid template. In some cases, this agent may comprise one or more amines, primary amines, secondary amines, polyamines such as DMED, piperidine, AP endonucleases, or any combination thereof.

In some embodiments, the kit of the present invention may contain one or more reagents for producing blunt ends from the double stranded products generated by the extension reaction. For example, the kit may contain one or more of single stranded DNA specific exonucleases including but not limited to exonuclease 1 or exonuclease 7; a single stranded DNA specific endonucleases such as mung bean exonuclease or S1 exonuclease, one or more polymerases such as for example T4 DNA polymerase or Klenow polymerase, or any mixture thereof. Alternatively, the kit may contain one or more single stranded DNA specific exonucleases, endonucleases and one or more polymerases, wherein the reagents are not provided as a mixture. Additionally, the reagents for producing blunt ends may comprise dNTPs.

In some embodiments, the kit of the present invention may contain one or more reagents for preparing the double stranded products for ligation to adaptor molecules. For example, the kit may contain dATP, dCTP, dGTP, dTTP, or any mixture thereof. In some cases, the kit may contain a polynucleotide kinase, such as for example T4 polynucleotide kinase. Additionally, the kit may contain a polymerase suitable for producing a 3' extension from the blunt ended double stranded DNA fragments. Suitable polymerases are included, for example, exo-Klenow polymerase.

In some embodiments, the kit of the present invention may contain one or more adaptor molecules such as any of the adaptor molecules provided herein. Suitable adaptor molecules include single or double stranded nucleic acid (DNA or RNA) molecules or derivatives thereof, stem-loop nucleic acid molecules, double stranded molecules comprising one or more single stranded overhangs of 1, 2, 3, 4, 5, 6, 7, 8, 9, 10 bases or longer, proteins, peptides, aptamers, organic molecules, small organic molecules, or any adaptor molecules known in the art that may be covalently or non-covalently attached, such as for example by ligation, to the double stranded DNA fragments.

In some embodiments, the kit of the present invention may contain one or more reagents for performing gap or fill-in repair on the ligation complex formed between the adaptors and the double stranded products of the present invention. The kit may contain a polymerase suitable for performing gap repair. Suitable polymerases are included, for example, Taq DNA polymerase.

The kit may further contain instructions for the use of the kit. For example, the kit may contain instructions for generating directional cDNA libraries or directional cDNA libraries representing a whole transcriptome useful for large scale analysis including but not limited to e.g., sequencing by synthesis, sequencing by hybridization, single molecule sequencing, nanopore sequencing, and sequencing by ligation, high density PCR, digital PCR, massively parallel Q-PCR, and characterizing amplified nucleic acid products generated by the methods of the invention, or any combination thereof. In some cases, the kit may contain instructions for generating a second strand comprising one or more modified nucleotides. The kit may further contain instructions for mixing the one or more reaction mixture components to generate one or more reaction mixtures suitable for the methods of the present invention. The kit may further contain instructions for hybridizing the one or more oligonucleotide primers to a nucleic acid template. The kit may further contain instructions for extending the one or more oligonucleotide primers with for example a polymerase. The kit may further contain instructions for cleaving the base portion of a modified nucleotide to generate an abasic site, with, for example, a glycosylase. The kit may further contain instructions for fragmenting a phosphodiester backbone at an abasic site to fragment the input nucleic acid template, with, for example, any of the suitable agents provided herein such as a polyamine. The kit may further contain instructions for purification of any of the products provided by any of the steps of the methods provided herein. The kit may further contain instructions for producing blunt ended fragments, for example by removing single stranded overhangs or filling in single stranded overhangs, with for example single stranded DNA specific exonucleases, polymerases, or any combination thereof. The kit may further contain instructions for phosphorylating the 5' ends of the double stranded DNA fragments produced by the methods of the present invention. The kit may further contain instructions for ligating one or more adaptor molecules to the double stranded DNA fragments of the present invention.

A kit will preferably include instructions for employing, the kit components as well the use of any other reagent not included in the kit. Instructions may include variations that can be implemented.

Products Based on the Methods of the Invention

Products based on the methods of the invention may be commercialized by the Applicants under the trade name Encore™, Ultra-low Encore™ or Encore Eukaryotic Stranded RNA-Seq. Encore is a trademark of NuGEN Technologies, Inc.

EXAMPLES

Example 1

Generation of a Directional cDNA Library

This example describes the generation of a directional cDNA library using conventional blunt-end ligation with modified duplex adaptors and 50 ng of poly(A)+ selected messenger RNA as a starting material. An overview of the end-end work-flow for the generation of the directional cDNA library is shown in FIG. 4.

First Strand Synthesis

First strand cDNA was generated using random hexamer priming. The first strand synthesis reaction was conducted using the Invitrogen SuperScript III Reverse Transcriptase kit, with 10 µM of random hexamers, 3.0 mM $MgCl_2$ and 1.0 mM dNTPs. The cDNA synthesis reaction was carried out in 10 µL volume, incubated at 40 degrees Celsius for 60 minutes and chilled to 4 degrees Celsius.

Second Strand Synthesis with dUTP Incorporation

Second strand synthesis was performed using the New England Biolabs NEBNext Second Strand Synthesis Module, where the Second Strand Synthesis (dNTP-free) Reaction Buffer was supplemented with dNTP mix containing 0.2 mM of dATP, dCTP and dGTP, and 0.54 mM dUTP. RNAse H-mediated nick translation was carried out by adding 65 µL of second strand synthesis master mix and incubating for one hour at 16 degrees Celsius. The reaction was stopped by adding 45 µL of 25 mM EDTA.

Fragmentation and Purification of cDNA Fragments

The 120 µL second strand synthesis reaction was subjected to acoustic fragmentation using the Covaris S-series System according to the manufacturer's instructions, using the manufacturer recommended settings to produce fragmented DNA with an average fragment size of 150-200 bases. Fragmented DNA was concentrated using QiAquick PCR purification kit, according to the manufacturer's instructions. The fragmented and concentrated DNA was quantitated and run on Agilent Bioanalyzer DNA 1000 chip to ensure fragment distribution of 150-200 bp length.

End Repair

The ends of the fragmented cDNA were repaired to generate blunt ends with 5' phosphates and 3' hydroxyls. End repair of the fragmented DNA was performed according to the Encore™ Ultra Low Input NGS Library System I User Guide instructions using End Repair Master Mix.

Ligation with dU Marked Adaptors

Duplex adaptors were ligated to blunt-ended cDNA fragments according to the Encore™ Ultra Low Input NGS Library System I User Guide Instructions, with the exception that the Ligation Adaptor Mix contained one adaptor where the ligation strand of the adaptor had at least one dU incorporated into it.

Nick Repair/Adaptor Fill-in

Ligation of unphosphorylated adaptors leaves a single-strand nick that must be repaired prior to strand selection and amplification. To fill in the adaptor sequence and generate full-length double-stranded DNA (dsDNA), the reaction mix was heated at 72 degrees Celsius, resulting in the extension of the 3' end of the cDNA insert by Taq DNA polymerase (thereby filling in the adaptor sequence), and the melting of the unligated adaptor strand. The repaired dsDNA fragments with ligated adaptors were then purified using Agencourt RNAClean XP Beads, according to the Encore™ Ultra Low Input NGS Library System I User Guide Instructions.

Strand Selection with UDG/APE I Treatment

Uridine digestion was performed with 1 unit of UNG and 1,000 units of APE I at 37° C. for 20 minutes. Incorporation of dUTP into one strand of the cDNA insert and the ligation strand of one of the two adaptors allowed for selective removal of the products with the undesired adaptor orientation. Consequently, a polynucleotide strand with incorporated dUTP that is treated with UNG/APE I was unable to undergo amplification by a polymerase.

Library Amplification

To produce a final directional cDNA library, the UNG-selected fragments were amplified by PCR according to the Library Amplification Protocol in the Encore™ Ultra Low Input NGS Library System I User Guide.

Example 2

RNA Strand Retention Efficiency

In this example, strand retention efficiency using the methods of the invention was validated experimentally by assessing the strand bias of sequence reads that map to the coding exons of human mRNAs. A directional cDNA library, as described in the invention, and a non-directional cDNA library (control) were generated from poly (A)+RNA isolated from human whole brain. Single end 40 nucleotide reads were generated using the Illumina Genome Analyzer II. Strand retention efficiency was measured by comparing the strand biases of sequence reads from the directional library and the non-directional control library. The results are presented in FIG. 3. After dUTP incorporation and UNG/APE I digestion of the strand with the undesired P2/P1 adaptor orientation, 98% of reads from the directional cDNA library aligned to the correct (antisense) strand orientation, as compared to approximately 50% of reads in a non-directional control cDNA library.

Example 3

RNA Strand Retention Efficiency

In this example, strand retention efficiency using the methods of the invention was validated experimentally by assessing the strand bias of sequence reads that map to the 5' UTR and 3' UTR regions of human mRNAs. Strand retention efficiency was measured as described in Example 2. The corresponding strand retentions for the directional library were 95% and 98% in the 5' UTR and 3' UTR regions, respectively, and 39% and 50% for the non-directional library.

Example 4

Generation of a Directional cDNA Library

This example describes the generation of a directional cDNA library using conventional blunt-end ligation with modified duplex adaptors and 50 ng of poly(A)+ selected messenger RNA as a starting material.

First Strand Synthesis with dUTP Incorporation

First strand cDNA was generated using random hexamer priming. The first strand synthesis reaction was conducted using the Invitrogen SuperScript III Reverse Transcriptase kit, with 10 µM of random hexamers, 3.0 mM $MgCl_2$ and supplemented with dNTP mix containing dATP, dCTP, dGTP, and dUTP in place of dTTP. The cDNA synthesis reaction was carried out in 10 µL volume, incubated at 40 degrees Celsius for 60 minutes and chilled to 4 degrees Celsius. After first strand synthesis, non-incorporated dNTPs were removed prior to second strand synthesis.

Second Strand Synthesis

Second strand synthesis was performed using the New England Biolabs NEBNext Second Strand Synthesis Module, where the Second Strand Synthesis (dNTP-free) Reaction Buffer was supplemented with dNTP mix containing dATP, dCTP, dGTP, and dTTP. RNAse H-mediated nick translation was carried out by adding 65 µL of second strand synthesis master mix and incubating for one hour at 16 degrees Celsius. The reaction was stopped by adding 45 µL of 25 mM EDTA.

Fragmentation and Purification of cDNA Fragments

The 120 µL second strand synthesis reaction was subjected to acoustic fragmentation using the Covaris S-series System according to the manufacturer's instructions, using the manufacturer recommended settings to produce fragmented DNA with an average fragment size of 150-200 bases. Fragmented DNA was concentrated using QIAquick PCR purification kit, according to the manufacturer's instructions. The fragmented and concentrated DNA was quantitated and run on Agilent Bioanalyzer DNA 1000 chip to ensure fragment distribution of 150-200 bp length.

End Repair

The ends of the fragmented cDNA were repaired to generate blunt ends with 5' phosphates and 3' hydroxyls. End repair of the fragmented DNA was performed according to the Encore™ Ultra Low Input NGS Library System I User Guide instructions using End Repair Master Mix.

Ligation with dU Marked Adaptors

Duplex adaptors were ligated to blunt-ended cDNA fragments according to the Encore™ Ultra Low Input NGS Library System I User Guide Instructions, with the exception that the Ligation Adaptor Mix contained one adaptor where the ligation strand of the adaptor had at least one dU incorporated into it.

Nick Repair/Adaptor Fill-in

Ligation of unphosphorylated adaptors leaves a single-strand nick that must be repaired prior to strand selection and amplification. To fill in the adaptor sequence and generate full-length double-stranded DNA (dsDNA), the reaction mix was heated at 72 degrees Celsius, resulting in the extension of the 3' end of the cDNA insert by Taq DNA polymerase (thereby filling in the adaptor sequence), and the melting of the mitigated adaptor strand. The repaired dsDNA fragments with ligated adaptors were then purified using Agencourt RNAClean XP Beads, according to the Encore™ Ultra Low Input NGS Library System 1 User Guide Instructions.

Strand Selection with UDG/APE I Treatment

Uridine digestion was performed with 1 unit of UNG and 1,000 units of APE I at 37° C. for 20 minutes. Incorporation of dUTP into one strand of the cDNA insert and the ligation strand of one of the two adaptors allowed for selective removal of the products with the undesired adaptor orientation. Consequently, a polynucleotide strand with incorporated dUTP that is treated with UNG/APE I was unable to undergo amplification by a polymerase.

Library Amplification

To produce a final directional cDNA library, the UNG-selected fragments were amplified by PCR according to the Library Amplification Protocol in the Encore™ Ultra Low Input NGS Library System I User Guide.

What is claimed is:

1. A method for construction of a directional cDNA library, the method comprising:
    a. reverse transcribing an RNA sample to generate a first strand cDNA;
    b. generating a second strand cDNA from the first strand cDNA, wherein the generating the second strand cDNA comprises incorporating a modified dNTP during the generating the second strand cDNA, synthesis and incorporated into the second strand, thereby generating a double-stranded cDNA;
    c. performing end repair on the double-stranded cDNA;
    d. ligating two adaptors to the double-stranded cDNA, wherein each of the two adaptors comprise a ligation strand and a non-ligation strand, wherein only one of the two adaptors has the modified dNTP incorporated into the ligation strand of the adaptor, wherein the ligation strand of each of the two adaptors is configured to ligate to a 5' end of the double-stranded cDNA;
    e. extending each 3' end of the double-stranded cDNA with a polymerase, wherein the ligation strand of one of the two adaptors is used as a template; and
    f. selectively cleaving the second strand cDNA and the adaptor that has the modified dNTP using a cleavage agent, thereby generating a directional cDNA library comprising the first strand cDNA.

2. The method of claim 1, wherein the modified dNTP comprises dUTP.

3. The method of claim 1, wherein the method further comprises fragmenting the double-stranded cDNA prior to step (c).

4. The method of claim 1, wherein step (f) comprises cleaving a base portion of the modified dNTP, thereby forming an abasic site.

5. The method of claim 4, further comprising cleaving a phosphodiester backbone at the abasic site.

6. The method of claim 4, wherein the cleaving the base portion of the modified dNTP comprises use of an enzyme.

7. The method of claim 5, wherein the cleaving the phosphodiester backbone at the abasic site comprises use of an enzyme, chemical agent, or heat.

8. The method of claim 7, wherein the cleaving the phosphodiester backbone at the abasic site comprises use of an enzyme, wherein the enzyme is an endonuclease.

9. The method of claim 8, wherein the endonuclease is an apurinic/apyrimidinic endonuclease (APE).

10. The method of claim 6, wherein the enzyme comprises a glycosylase.

11. The method of claim 10, wherein the glycosylase is uracil-N-glycosylase (UNG) or uracil DNA glycosylase (UDG).

12. The method of claim 7, wherein the cleaving the phosphodiester backbone at the abasic site comprises use of a chemical agent, wherein the chemical agent comprises a primary amine.

13. The method of claim 7, wherein the cleaving the phosphodiester backbone at the abasic site comprises use of a chemical agent, wherein the chemical agent comprises a polyamine.

14. The method of claim 13, wherein the polyamine comprises N,N-dimethylethylenediamine (DMED).

15. The method of claim 1, wherein the cleavage agent comprises a glycosylase and a polyamine.

16. The method of claim 1, wherein the cleavage agent comprises a glycosylase and an APE.

17. The method of claim 1, further comprising amplifying the directional cDNA library, thereby generating amplified products.

18. The method of claim 17, wherein the amplification of the directional cDNA library comprises polymerase chain reaction (PCR), strand displacement amplification (SDA), multiple displacement amplification (MDA), rolling circle amplification (RCA), single primer isothermal amplification (SPIA), or ligase chain reaction (LCR).

19. The method of claim 18, wherein the amplification comprises PCR.

20. The method of claim 18, wherein the amplification comprises SPIA.

21. The method of claim 17, further comprising sequencing the amplified products.

22. The method of claim 21, wherein the sequencing comprises next generation sequencing.

23. The method of claim 1, further comprising cleaving the RNA sample following reverse transcription.

24. The method of claim 23, wherein cleaving the RNA sample comprises exposing the RNA sample to an RNase following reverse transcription.

25. The method of claim 24, wherein the RNase is RNase H.

26. The method of claim 23, wherein cleaving the RNA sample comprises exposing the RNA sample to heat or chemical treatment.

27. The method of claim 1, further comprising reducing or depleting non-desired nucleic acid sequences from the directional cDNA library.

28. The method of claim 27, wherein the non-desired nucleic acid sequences are ribosomal RNA (rRNA) sequences.

29. A method for construction of a directional cDNA library comprising:
   a. generating first and second strand cDNA from template RNA, wherein the generating either the first strand cDNA or the second strand cDNA comprises incorporating a modified dNTP, thereby generating a double stranded cDNA comprising the first strand cDNA hybridized to the second strand cDNA, wherein either the first strand cDNA or the second strand cDNA of the double stranded cDNA comprises the modified dNTP;
   b. performing end repair on the double-stranded cDNA;
   c. ligating two adaptors to the double-stranded cDNA, wherein each of the two adaptors comprise a ligation strand and a non-ligation strand, wherein only one of the two adaptors comprises the modified dNTP incorporated into the ligation strand of the adaptor, wherein the ligation strand of each of the two adaptors is configured to ligate to a 5' end of the double-stranded cDNA;
   d. extending each 3' end of the double stranded cDNA with a polymerase, wherein the ligation strand of one of the two adaptors is used as template; and
   e. selectively cleaving the first or the second strand of the double stranded cDNA and the adaptor that has the modified dNTP by using a cleavage agent, thereby generating a directional cDNA library comprising the first strand cDNA or the second strand cDNA.

30. The method of claim 1, wherein the incorporating a modified dNTP comprises replacing at least one of dATP, dCTP, dGTP or dTTP with the modified dNTP.

* * * * *